(12) United States Patent
Stangeland et al.

(10) Patent No.: US 8,637,568 B2
(45) Date of Patent: Jan. 28, 2014

(54) SEROTONIN REUPTAKE INHIBITORS

(71) Applicants: Eric L. Stangeland, Pacifica, CA (US); Lori Jean Van Orden, San Francisco, CA (US); Daisuke Roland Saito, San Mateo, CA (US)

(72) Inventors: Eric L. Stangeland, Pacifica, CA (US); Lori Jean Van Orden, San Francisco, CA (US); Daisuke Roland Saito, San Mateo, CA (US)

(73) Assignee: Theravance, Inc., South San Francisco, CA (US)

(*) Notice: Subject to any disclaimer, the term of this patent is extended or adjusted under 35 U.S.C. 154(b) by 0 days.

(21) Appl. No.: 13/936,312

(22) Filed: Jul. 8, 2013

(65) Prior Publication Data
US 2013/0296322 A1 Nov. 7, 2013

Related U.S. Application Data

(62) Division of application No. 13/308,844, filed on Dec. 1, 2011, now Pat. No. 8,501,964.

(60) Provisional application No. 61/419,346, filed on Dec. 3, 2010.

(51) Int. Cl.
*A61K 31/40* (2006.01)
*C07D 207/08* (2006.01)

(52) U.S. Cl.
USPC .......................................... 514/428; 548/566

(58) Field of Classification Search
USPC .......................................... 514/428; 548/566
See application file for complete search history.

(56) References Cited

U.S. PATENT DOCUMENTS

| | | | |
|---|---|---|---|
| 3,634,437 A | 1/1972 | Todd | |
| 4,229,449 A | 10/1980 | Melloni et al. | |
| 4,243,807 A | 1/1981 | Friebe et al. | |
| 5,023,269 A | 6/1991 | Robertson et al. | |
| 5,037,841 A | 8/1991 | Schohe et al. | |
| 5,614,518 A | 3/1997 | Leeson et al. | |
| 6,518,284 B2 | 2/2003 | Orjales Venero et al. | |
| 7,294,637 B2 | 11/2007 | Aquila et al. | |
| 7,317,011 B2 | 1/2008 | Wong et al. | |
| 7,378,436 B2 | 5/2008 | Fish et al. | |
| 7,384,941 B2 | 6/2008 | Walter et al. | |
| 7,888,386 B2 | 2/2011 | Stangeland et al. | |
| 7,994,209 B2 | 8/2011 | Stangeland et al. | |
| 8,273,786 B2 | 9/2012 | Stangeland et al. | |
| 8,471,040 B2 | 6/2013 | Stangeland et al. | |
| 2002/0151712 A1 | 10/2002 | Lin et al. | |
| 2005/0245519 A1 | 11/2005 | Barta et al. | |
| 2005/0250775 A1 | 11/2005 | Fish et al. | |
| 2007/0015786 A1 | 1/2007 | Allen et al. | |
| 2007/0072859 A1 | 3/2007 | Boulet et al. | |
| 2007/0265306 A1 | 11/2007 | Orjales Venero et al. | |
| 2009/0215857 A1 | 8/2009 | Lanni et al. | |
| 2010/0120858 A1 | 5/2010 | Caprathe et al. | |
| 2010/0261762 A1 | 10/2010 | Dreyfus et al. | |
| 2010/0267743 A1 | 10/2010 | Stangeland et al. | |

OTHER PUBLICATIONS

Fish et al., "N-benzyl-N-(tetrahydro-2H-pyran-4-yl)pyrrolidin-3-amines as selective dual serotonin/noradrenaline reuptake inhibitors", Bioorganic & Medicinal Chemistry Letters, 17, pp. 2022-2025, 2007.

Fish et al., "Design and synthesis of morpholine derivatives. SAR for dual serotonin & noradrenaline reuptake inhibition", Bioorganic & Medicinal Chemistry Letters, 18, pp. 2562-2566, 2008.

Fish et al., "Derivatives of (3S)-N-(biphenyl-2-ylmethyl)pyrrolidin-3-amine as selective noradrenaline reuptake inhibitors: Reducing P-gp mediated efflux by modulation of H-bond acceptor capacity", Bioorganic & Medicinal Chemistry Letters, 18, pp. 4355-4359, 2008.

Fish et al., "4-Piperidines and 3-pyrrolidines as dual serotonin and noradrenaline reuptake inhibitors: Design, synthesis and structure-activity relationships", Bioorganic & Medicinal Chemistry Letters, 19, pp. 2829-2834, 2009.

Melloni et al., "Potential antidepressant agents. Alpha-aryloxy-benzyl derivatives of ethanolamine and morpholine", European Journal of Medicinal Chemistry, 19(3), pp. 235-242, 1984.

Murphy et al., "The Synthesis and Biological Evaluation of Novel Series of Nitrile-containing Fluoroquinolones as Antibacterial Agents", Bioorganic & Medicinal Chemistry Letters, 17, pp. 2150-2155 (2007).

(Continued)

*Primary Examiner* — Robert Havlin
(74) *Attorney, Agent, or Firm* — Jeffrey A. Hagenah; Shelley Eberle

(57) ABSTRACT

In one aspect, the invention relates to compounds of formula I:

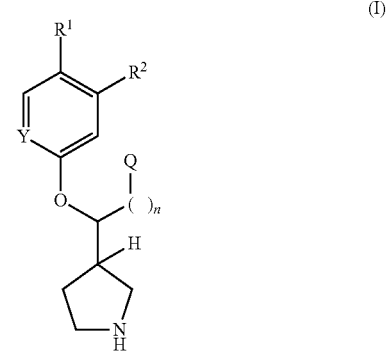

(I)

where Y, $R^1$, $R^2$, n, and Q are as defined in the specification, or a pharmaceutically acceptable salt thereof. The compounds of formula I are serotonin reuptake inhibitors. In another aspect, the invention relates to pharmaceutical compositions comprising such compounds; methods of using such compounds; and processes and intermediates for preparing such compounds.

16 Claims, No Drawings

(56) References Cited

OTHER PUBLICATIONS

Orjales et al., "Synthesis and binding studies of new [(aryl)(aryloxy)methyl]piperidine derivatives and related compounds as potential antidepressant drugs with high affinity for serotonin (5-HT) and norepinephrine (NE) transporters", Journal of Medicinal Chemistry, 46, pp. 5512-5532, 2003.

International Search Report for PCT/US2011/062813 dated Feb. 21, 2012.

Abou-Raya et al., "Duloxetine for the management of pain in older adults with knee osteoarthritis: randomised placebo-controlled trial", Age Ageing, 41(5):642-652 (Sep. 2012) (abstract only).

Amsterdam et al., "Safety and efficacy of s-citalopram in patients with co-morbid major depression and diabetes mellitus", Neuropsychobiology, 54:208-214 (2006).

Gil-Ad et al., "Evaluation of the potential anti-cancer activity of the antidepressant sertraline in human colon cancer cell lines and in colorectal cancer-xenografted mice", International Journal of Oncology, 33:277-286 (2008).

Moore et al., "Interaction of a selective serotonin reuptake inhibitor with insulin in the control of hepatic glucose uptake in conscious dogs", Am J Physiol Endocrinol Metab, 288:E-556-E563 (2005).

Roumestan et al., "Anti-inflammatory properties of desipramine and fluoxetine", Respiratory Research, 8:35 (2007).

Sacre et al., "Fluoxetine and citalopram exhibit potent antiinflammatory activity in human and murine models of rheumatoid arthritis and inhibit toll-like receptors", Arthritis & Rheumatism, 62(3):683-693 (Mar. 2010).

Yadav et al., "Pharmacological inhibition of gut-derived serotonin synthesis is a potential bone anabolic treatment for osteoporosis", Nature Medicine, pp. 1-7 (2010).

SEROTONIN REUPTAKE INHIBITORS

CROSS-REFERENCE TO RELATED APPLICATIONS

This application is a divisional application of U.S. Ser. No. 13/308,844, filed Dec. 1, 2011, now allowed, which claims the benefit of U.S. Provisional Application No. 61/419,346, filed on Dec. 3, 2010; the entire disclosures of which are incorporated herein by reference.

BACKGROUND OF THE INVENTION

1. Field of the Invention

The present invention relates to and 2-phenoxy-2-pyrrolidin-3-yl-ethylsulfonamide and 2-phenoxy-2-pyrrolidin-3-ylethanesulfonic acid amide compounds having activity as serotonin (5-HT) reuptake inhibitors and, in one embodiment, having the characteristic of being selectively restricted from the central nervous system. The invention also relates to pharmaceutical compositions comprising such compounds, processes, and intermediates for preparing such compounds and methods of using such compounds to treat pulmonary arterial hypertension and other ailments.

2. State of the Art

Progressive increase in pulmonary vascular resistance (PVR) restricts blood flow and causes pulmonary arterial hypertension (PAH), which ultimately leads to right heart failure and death. PAH includes primary pulmonary hypertension and pulmonary hypertension associated with collagen vascular diseases, congenital systemic-to-pulmonary shunts, portal hypertension, and HIV infection. The causes of increased PVR include vasoconstriction and vascular remodeling (increased VSMC proliferation/migration/fibrosis and narrowing of vascular lumen). The goal of therapy is to improve symptoms and exercise capacity, and, ultimately, survival. Current drug therapies include treatment with prostanoids, calcium channel blockers, endothelin receptor antagonists, and PDE-5 inhibitors. Unfortunately, these drugs typically only provide a symptomatic benefit. Therefore, there is an unmet need for drugs that can impact PAH disease progression.

There is preclinical evidence for a role of both serotonin (5-hydroxytrypamine, 5-HT) and the serotonin transporter (SERT) in PAH. SERT is highly expressed in human lung and 5-HT, via interaction with SERT, stimulates proliferation of human pulmonary vascular smooth muscle cells (HPVSM). The proliferative effects of 5-HT are exaggerated in HPVSM from PAH patients. Serotonin selective reuptake inhibitors (SSRIs) have been shown to prevent or reverse PAH in animal models (Zhu et al. (2009) *Clinical and Experimental Pharmacology and Physiology* 36(8): e1-e5), and the overexpression and deficiency of SERT increases and decreases susceptibility to hypoxia-induced PAH in mice, respectively (Shah et al. (2009) *Chest* 136(3):694-700).

While there are numerous SSRIs available on the market, most are directed to treating diseases such as depression, anxiety, and other mental health conditions, and thus are designed to primarily enter the central nervous system (CNS). Unfortunately, this CNS activity is often associated with adverse effects such as nausea, sexual distraction, insomnia, somnolence and anxiety. Treatment of diseases such as PAH do not require CNS activity. Therefore, it is desirable to design a therapeutic agent that has SERT inhibition activity yet is peripherally selective, thus potentially avoiding or reducing centrally mediated side effects. This invention is directed to that need.

SUMMARY OF THE INVENTION

The present invention provides novel compounds that have been found to possess serotonin reuptake inhibition activity. In one embodiment, the compounds of the invention are peripherally selective such that they exist predominantly in the periphery as compared to the central nervous system. Accordingly, compounds of the invention are expected to be useful and advantageous as therapeutic agents for those diseases and disorders that can be treated by inhibition of the serotonin transporter in the absence of CNS activity, such as pulmonary arterial hypertension (PAH) and anti-platelet therapy.

One aspect of the invention relates to a compound of formula I:

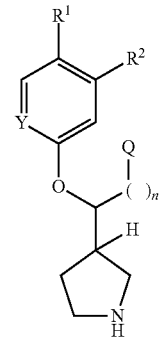

(I)

where:
Y is —CH— or —N—;
$R^1$ is selected from halo; —$C_{1-6}$alkyl optionally substituted with 1 to 5 fluoro atoms; —O—$C_{1-6}$alkyl optionally substituted with 1 to 5 fluoro atoms; —$C_{0-1}$alkylene-phenyl; —O—$C_{0-3}$alkylene-phenyl; —$SO_2$—$C_{1-6}$alkyl; —C(O)$NH_2$; and —$NO_2$;
$R^2$ is selected from hydrogen, halo, and —CN;
n is an integer from 1 to 3;
Q is selected from —$NR^3SO_2R^4$ and —$SO_2NR^5R^6$;
$R^3$ is selected from hydrogen, —$C_{1-6}$alkyl, and —C(O) $C_{1-6}$ alkyl;
$R^4$ is selected from —$C_{1-6}$alkyl, —$C_{3-6}$cycloalkyl; —$NR^7R^8$; —$CH_2SO_2$—$C_{1-6}$alkyl; pyrazole optionally substituted with —$CH_3$; triazole, morpholine; benzoxadiazole; and phenyl optionally substituted with $R^9$; where $R^7$ and $R^8$ are independently selected from hydrogen and —$C_{1-6}$alkyl; and $R^9$ is selected from —CN, —COOH, —$NO_2$, —$C_{0-2}$alkylene-O—$C_{1-6}$alkyl, —C(O)$NR^7R^8$; —$NR^7C(O)$—$C_{1-6}$alkyl; —$SO_2$—$C_{1-6}$ alkyl, —$SO_2$—$NR^7R^8$, and a nitrogen-containing heteroaryl optionally substituted with 1 or 2-$CH_3$ groups;
$R^5$ is selected from hydrogen and —$C_{1-6}$alkyl;
$R^6$ is selected from hydrogen, —$C_{1-6}$alkyl, and benzyl; and or a pharmaceutically acceptable salt thereof.

Another aspect of the invention relates to compounds of formula I having a configuration selected from formulas a, b, c, and d, or enriched in a stereoisomeric form having such configuration.

Yet another aspect of the invention relates to pharmaceutical compositions comprising a pharmaceutically acceptable carrier and a compound of the invention. Such compositions may optionally contain other active agents. Accordingly, in yet another aspect of the invention, a pharmaceutical composition comprises a compound of the invention, a second active agent, and a pharmaceutically acceptable carrier. Another aspect of the invention relates to a combination of active agents, comprising a compound of the invention and a second active agent. The compound of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising a compound of formula I or a pharmaceutically acceptable salt thereof and a first pharmaceutically acceptable carrier; and a second pharmaceutical composition comprising a second active agent and a second pharmaceutically acceptable carrier. The invention also relates to a kit containing such pharmaceutical compositions, for example where the first and second pharmaceutical compositions are separate pharmaceutical compositions.

Compounds of the invention possess serotonin reuptake inhibition activity and are therefore expected to be useful as therapeutic agents for treating patients suffering from a disease or disorder that is treated by the inhibition of the serotonin transporter primarily in the periphery as compared to the CNS. Thus, one aspect of the invention relates to a method of treating a disease selected from pulmonary arterial hypertension, gastrointestinal disorders, cancer, rheumatoid arthritis, osteoarthritis, osteoporosis, and diabetes, comprising administering to a patient a therapeutically effective amount of a compound of the invention. In one specific aspect, the invention relates to a method of treating pulmonary arterial hypertension. Another aspect of the invention relates to a method of treating a patient that is in need of anti-platelet therapy, comprising administering to a patient a therapeutically effective amount of a compound of the invention.

Still another aspect of the invention relates to a method for inhibiting serotonin reuptake in a mammal comprising administering to the mammal, a serotonin transporter-inhibiting amount of a compound of the invention.

Among the compounds of formula I, compounds of particular interest are those having a serotonin reuptake inhibition $pIC_{50}$ value $\geq 5.0$, particularly those having a $pIC_{50 \geq 7.0}$, and even more particularly those having a $pIC_{50} \geq 8.0$.

Since compounds of the invention possess serotonin reuptake inhibitory activity, they are also useful as research tools. Accordingly, one aspect of the invention relates to a method of using a compound of the invention as a research tool, comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a serotonin reuptake assay. Still another aspect of the invention relates to a method of studying a biological system or sample comprising serotonin transporters, the method comprising: (a) contacting the biological system or sample with a compound of the invention; and (b) determining the effects caused by the compound on the biological system or sample.

The invention also relates to processes and intermediates useful for preparing compounds of the invention. Accordingly, one aspect of the invention relates to a process for preparing a compound of formula I, the process comprising deprotecting a compound of formula II:

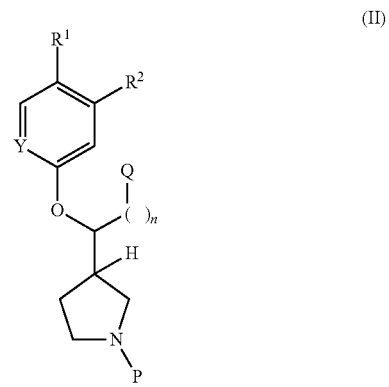

(II)

to provide a compound of formula I, or a salt thereof; where Y, $R^1$, $R^2$, n, and Q are as defined for formula I, and P is an amino-protecting group. In other aspects, the invention relates to novel intermediates used in such processes. In one aspect of the invention, such novel intermediates have formula II.

Yet another aspect of the invention relates to the use of compounds of the invention for the manufacture of medicaments, especially for the manufacture of medicaments useful for treating pulmonary arterial hypertension, for anti-platelet therapy, or for inhibiting serotonin reuptake in a mammal. Still another aspect of the invention relates to the use of compounds of the invention as research tools. Other aspects and embodiments of the invention are disclosed herein.

DETAILED DESCRIPTION OF THE INVENTION

Definitions

When describing the compounds, compositions, methods and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group that may be linear or branched. Unless otherwise defined, such alkyl groups typically contain from 1 to 10 carbon atoms and include, for example, —$C_{1-2}$alkyl, —$C_{1-3}$alkyl, —$C_{1-4}$alkyl, —$C_{1-6}$alkyl, and —$C_{1-6}$alkyl. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" means a divalent saturated hydrocarbon group that may be linear or branched. Unless otherwise defined, such alkylene groups typically contain from 0 to 10 carbon atoms and include, for example, —$C_{0-1}$alkylene-, —$C_{0-3}$alkylene-, and —$C_{1-2}$alkylene-. Representative alkylene groups include, by way of example: methylene; ethylene; propylene, —$(CH_2)_3$—, and branched —$C_3$alkylene such as —$CH(CH_3)$—$CH_2$—; butylene, —$(CH_2)_4$—, and branched —$C_4$alkylene such as —$CH(CH_3)$—$(CH_2)_2$— and —$CH_2$—$CH(CH_3)$—$CH_2$—; pentylene, —$(CH_2)_5$—, and branched —$C_5$alkylene such as —$CH(CH_3)$—$(CH_2)_3$— and —$CH_2$—$C(CH_3)_2$—$CH_2$—; and the like. It is understood that when the alkylene term includes zero carbons such as —$C_{0-1}$alkylene-, —$C_{0-2}$alkylene- or —$C_{0-3}$alkylene-, such terms are intended to include the absence of carbon atoms, that is, the alkylene group is not present except for a covalent bond attaching the groups separated by the alkylene term.

When a specific number of carbon atoms are intended for a particular term used herein, the number of carbon atoms is shown preceding the term as subscript. For example, the term "—$C_{1-6}$alkyl" means an alkyl group having from 1 to 6 carbon atoms, and the term "—$C_{0-3}$alkylene-" means an alkylene group having from 0 to 3 carbon atoms, where the carbon atoms are in any acceptable configuration.

The term "cycloalkyl" means a monovalent saturated carbocyclic hydrocarbon group. Unless otherwise defined, such cycloalkyl groups typically contain from 3 to 10 carbon atoms and include, for example, —$C_{3-6}$cycloalkyl. Representative cycloalkyl groups include, by way of example, cyclopropyl, cyclobutyl, cyclopentyl, cyclohexyl and the like.

The term "halo" means fluoro, chloro, bromo, and iodo.

As used herein, the phrase "having the formula" or "having the structure" is not intended to be limiting and is used in the same way that the term "comprising" is commonly used.

The term "nitrogen-containing heteroaryl" means a group having a single ring or two fused rings containing from 5 to 10 total ring atoms and having at least one nitrogen atom. Additional heteroatoms (typically 1 to 4 heteroatoms) selected from nitrogen, oxygen or sulfur may also be present. Nitrogen-containing heteroaryls" include, for example, —$C_{1-9}$heteroaryl and —$C_{5-9}$heteroaryl, and representative groups include, by way of example, pyrrole (e.g., 3-pyrrolyl and 2H-pyrrol-3-yl), imidazole (e.g., 2-imidazolyl), triazole (e.g., 1,2,3-triazolyl and 1,2,4-triazolyl), pyrazole (e.g., 1H-pyrazol-3-yl), oxazole (e.g. 2-oxazolyl), isoxazole (e.g., 3-isoxazolyl), thiazole (e.g., 2-thiazolyl and 4-thiazolyl), and isothiazole (e.g., 3-isothiazolyl), pyridine (e.g., 2-pyridyl, 3-pyridyl, and 4-pyridyl), pyridylimidazole, pyridyltriazole, pyrazine, pyridazine (e.g., 3-pyridazinyl), pyrimidine (e.g., 2-pyrimidinyl), tetrazole, triazine (e.g., 1,3,5-triazinyl), indole (e.g., 1H-indol-2-yl, 1H-indol-4-yl and 1H-indol-5-yl), benzimidazole, benzoxazole, benzothiazole, benzotriazole, benzoxadiazole (e.g., benzo[1,2,5]oxadiazole), quinoline (e.g., 2-quinolyl), isoquinoline, quinazoline, quinoxaline and the like.

The term "optionally substituted" means that group in question may be unsubstituted or it may be substituted one or several times, such as 1 to 3 times or 1 to 5 times. For example, an alkyl group that is "optionally substituted" with 1 to 5 fluoro atoms, may be unsubstituted, or it may contain 1, 2, 3, 4, or 5 fluoro atoms.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, and an acidic moiety such as a carboxylic acid, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like.

Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "therapeutically effective amount" means an amount sufficient to effect treatment when administered to a patient in need thereof, i.e., the amount of drug needed to obtain the desired therapeutic effect. For example, a therapeutically effective amount for treating pulmonary arterial hypertension is an amount of compound needed to, for example, reduce, suppress, eliminate, or prevent the symptoms of pulmonary arterial hypertension or to treat the underlying cause of pulmonary arterial hypertension. On the other hand, the term "effective amount" means an amount sufficient to obtain a desired result, which may not necessary be a therapeutic result. For example, when studying a system comprising a serotonin transporter, an "effective amount" may be the amount needed to inhibit serotonin reuptake.

The term "treating" or "treatment" as used herein means the treating or treatment of a disease or medical condition (such as pulmonary arterial hypertension) in a patient, such as a mammal (particularly a human), that includes: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating pulmonary arterial hypertension" would include preventing pulmonary arterial hypertension from occurring, ameliorating pulmonary arterial hypertension, suppressing pulmonary arterial hypertension, and alleviating the symptoms of pulmonary arterial hypertension. The term "patient" is intended to include those mammals, such as humans, that are in need of treatment or disease prevention, that are presently being treated for disease prevention or treatment of a specific disease or medical condition, as well as test subjects in which compounds of the invention are being evaluated or being used in a assay, for example an animal model.

All other terms used herein are intended to have their ordinary meaning as understood by those of ordinary skill in the art to which they pertain.

In one aspect, this invention relates to novel compounds of formula I:

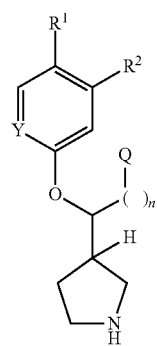

(I)

or a pharmaceutically acceptable salt thereof.

As used herein, the term "compound of the invention" includes all compounds encompassed by formula I such as the species embodied in formulas a-d, II, III, and IV and all other subspecies of such formulas. In addition, when the compound of the invention contain a basic or acidic group (e.g., amino or carboxyl groups), the compound can exist as a free base, free acid, or in various salt forms. All such salt forms are included within the scope of the invention. Accordingly, those skilled in the art will recognize that reference to a compound herein, for example, reference to a "compound of the invention" or a "compound of formula I" includes a compound of formula I as well as pharmaceutically acceptable salts of that compound unless otherwise indicated. Furthermore, solvates of compounds of formula I are included within the scope of this invention.

The compounds of formula I contain at least two chiral centers and therefore, these compounds may be prepared and used in various stereoisomeric forms. Accordingly, the invention also relates to racemic mixtures, pure stereoisomers (e.g., enantiomers and diastereoisomers), stereoisomer-enriched mixtures, and the like unless otherwise indicated. When a chemical structure is depicted herein without any stereochemistry, it is understood that all possible stereoisomers are encompassed by such structure. Thus, for example, the terms "compound of formula I," "compounds of formula II," and so forth, are intended to include all possible stereoisomers of the compound. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual enantiomers may be obtained by numerous methods that are well known in the art, including stereospecific synthesis, chiral chromatography using a suitable chiral stationary phase or support, or by chemically converting them into diastereoisomers, separating the diastereoisomers by conventional means such as chromatography or recrystallization, then regenerating the original enantiomers. Additionally, where applicable, all cis/trans or E/Z isomers (geometric isomers), tautomeric forms and topoisomeric forms of the compounds of the invention are included within the scope of the invention unless otherwise specified.

More specifically, compounds of formula I contain at least two chiral centers indicated by the symbols * and ** in the following formula:

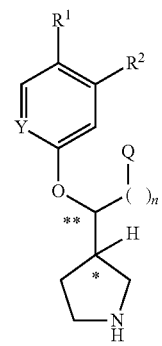

In one stereoisomer, both carbon atoms identified by the * and ** symbols have the (R) configuration. This embodiment of the invention is shown in formula a:

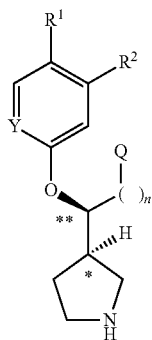

(a)

In this embodiment, compounds have the (R,R) configuration at the * and ** carbon atoms or are enriched in a stereoisomeric form having the (R,R) configuration at these carbon atoms.

In another stereoisomer, both carbon atoms identified by the * and ** symbols have the (S) configuration. This embodiment of the invention is shown in formula b:

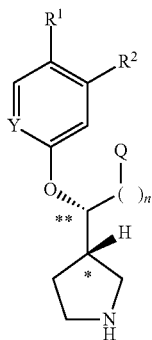

(b)

In this embodiment, compounds have the (S,S) configuration at the * and ** carbon atoms or are enriched in a stereoisomeric form having the (S,S) configuration at these carbon atoms.

In yet another stereoisomer, the carbon atom identified by the symbol * has the (S) configuration and the carbon atom identified by the symbol ** has the (R) configuration. This embodiment of the invention is shown in formula c:

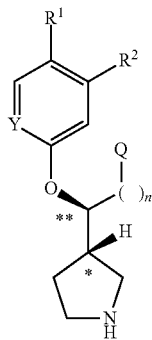

(c)

In this embodiment, compounds have the (S,R) configuration at the * and ** carbon atoms or are enriched in a stereoisomeric form having the (S,R) configuration at these carbon atoms.

In still another stereoisomer, the carbon atom identified by the symbol * has the (R) configuration and the carbon atom identified by the symbol ** has the (S) configuration. This embodiment of the invention is shown in formula d:

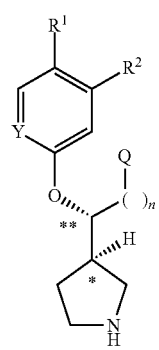

(d)

In this embodiment, compounds have the (R,S) configuration at the * and ** carbon atoms or are enriched in a stereoisomeric form having the (R,S) configuration at these carbon atoms.

Compounds of formula a and b are enantiomers and therefore, in separate aspects, this invention relates to each individual enantiomer (i.e., a or b), a racemic mixture of a and b, or an enantiomer-enriched mixture of a and b comprising predominately a or predominately b. Similarly, compounds of formula c and d are enantiomers and therefore, in separate aspects, this invention relates to each individual enantiomer (i.e., c or d), a racemic mixture of c and d, or an enantiomer-enriched mixture of c and d comprising predominately c or predominately d.

In some embodiments, in order to optimize the therapeutic activity of the compounds of the invention, e.g., to treat pulmonary arterial hypertension, it may be desirable that the carbon atoms identified by the * and ** symbols have a particular (R,R), (S,S), (S,R), or (R,S) configuration or are enriched in a stereoisomeric form having such configuration. For example, in one embodiment, the compounds of the invention have the (S,R) configuration of formula c or are enriched in a stereoisomeric form having the (S,R) configuration, and in another embodiment, the compounds of the invention have the (R,S) configuration of formula d, or are enriched in a stereoisomeric form having the (R,S) configuration. In other embodiments, the compounds of the invention are present as racemic mixtures, for example as a mixture of enantiomers of formula a and b, or as a mixture of enantiomers of formula c and d.

The compounds of the invention, as well as those compounds used in their synthesis may also include isotopically labeled compounds, i.e., where one or more atoms have been enriched with atoms having an atomic mass different from the atomic mass predominately found in nature. Examples of isotopes that may be incorporated into the compounds of formula I, for example, include, but are not limited to, $^2$H, $^3$H, $^{13}$C, $^{14}$C, $^{15}$N, $^{18}$O, $^{17}$O, $^{35}$S, $^{36}$Cl, and $^{18}$F. Of particular interest are compounds of formula I enriched in tritium or carbon-14 which can be used, for example, in tissue distribution studies; compounds of formula I enriched in deuterium especially at a site of metabolism resulting, for example, in compounds having greater metabolic stability; and compounds of formula I enriched in a positron emitting isotope, such as $^{11}C$, $^{18}F$, $^{15}O$ and $^{13}N$, which can be used, for example, in Positron Emission Topography (PET) studies.

The nomenclature used herein to name the compounds of the invention is illustrated in the Examples herein. This nomenclature has been derived using the commercially available AutoNom software (MDL, San Leandro, Calif.).

Representative Embodiments

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

In one aspect, this invention relates to compounds of formula I:

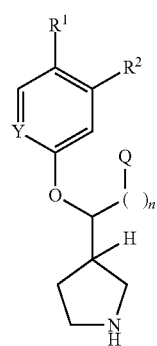

(I)

Y is —CH— or —N—. These embodiments can be depicted as formulas Ia and Ib, respectively:

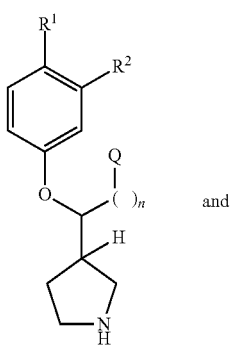

(Ia)

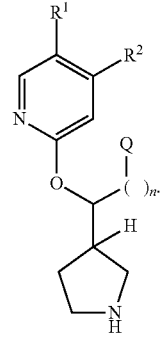

(Ib)

In one particular embodiment, Y is —CH—.

The $R^1$ moiety is selected from halo; —$C_{1-6}$alkyl optionally substituted with 1 to 5 fluoro atoms; —O—$C_{1-6}$alkyloptionally substituted with 1 to 5 fluoro atoms; —$C_{0-1}$alkylene-phenyl; —O—$C_{0-3}$alkylene-phenyl; —$SO_2$—$C_{1-6}$alkyl; —$C(O)NH_2$; and —$NO_2$. In one embodiment, $R^1$ is halo, examples of which include chloro and fluoro. In one embodiment, $R^1$ is —$C_{1-6}$alkyl, examples of which include methyl, ethyl, isopropyl, n-butyl, and t-butyl.

In one embodiment, $R^1$ is —$C_{1-6}$alkyl substituted with 1 to 5 fluoro atoms, examples of which include —$CH_2F$, —$CHF_2$, —$CF_3$, and —$CF_2CF_3$. In one embodiment, $R^1$ is —O—$C_{1-6}$alkyl, examples of which include —$OCH_3$ and —$OCH_2CH_3$. In one embodiment, $R^1$ is —O—$C_{1-6}$alkyl substituted with 1 to 5 fluoro atoms, examples of which include —$OCH_2F$, —$OCHF_2$, —$OCF_3$, and —$OCF_2CF_3$. In one embodiment, $R^1$ is —$C_{0-1}$alkylene-phenyl, i.e., phenyl and benzyl. In one embodiment, $R^1$ is —O—$C_{0-3}$alkylene-phenyl, examples of which include —O-phenyl and —O—$CH_2$-phenyl. In one embodiment, $R^1$ is —$SO_2$—$C_{1-6}$alkyl, examples of which include —$SO_2$—$CH_3$ and —$SO_2$—$CH_2CH_3$. In one embodiment, $R^1$ is —$C(O)NH_2$. In one embodiment, $R^1$ is —$NO_2$.

In one particular embodiment, $R^1$ is selected from —$C_{1-6}$ alkyl optionally substituted with 1 to 5 fluoro atoms, —O—$C_{1-6}$alkyl optionally substituted with 1 to 5 fluoro atoms, and —$NO_2$. In another particular embodiment, $R^1$ is —$C_{1-6}$alkyl optionally substituted with 1 to 5 fluoro atoms, more particularly, —$CF_3$.

The $R^2$ moiety is selected from hydrogen, halo, and —CN. In one embodiment, $R^2$ is hydrogen. In one embodiment, $R^2$ is halo, examples of which include chloro and fluoro.

In one embodiment, $R^2$ is cyano. In one particular embodiment, $R^2$ is selected from hydrogen and —CN. In another particular embodiment, $R^2$ is hydrogen.

In another particular embodiment, $R^1$ and $R^2$ combinations are as follows:

| $R^1$ | $R^2$ |
| --- | --- |
| —$CF_3$ | H |
| —$OCF_3$ | H |
| —$NO_2$ | H |
| Cl | —CN |
| —$CF_3$ | —CN |

The n integer is from 1 to 3. In one particular embodiment, n is 1.

The Q moiety is selected from —$NR^3SO_2R^4$ and —$SO_2NR^5R^6$. In one particular embodiment, Q is —NR³SO₂R⁴, which can be depicted as formula III:

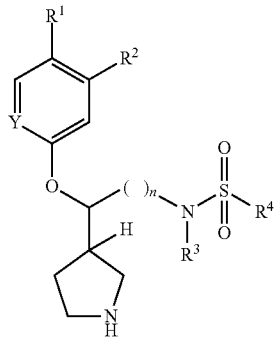

(III)

The R³ moiety is selected from hydrogen, —C₁₋₆alkyl, and —C(O)C₁₋₆alkyl. In one embodiment, R³ is hydrogen. In one embodiment, R³ is —C₁₋₆alkyl, examples of which include —CH₃, —CH₂CH₃, and so forth. In another embodiment, R³ is —C(O)C₁₋₆alkyl, examples of which include —C(O)CH₃. In still another embodiment, R³ is selected from hydrogen, —CH₃, and —C(O)CH₃.

The R⁴ moiety is selected from —C₁₋₆alkyl, —C₃₋₆cycloalkyl; —NR⁷R⁵; —CH₂SO₂—C₁₋₆alkyl; pyrazole optionally substituted with —CH₃; triazole, morpholine; benzoxadiazole; and phenyl optionally substituted with R⁹. In one embodiment, R⁴ is —C₁₋₆alkyl, examples of which include —CH₃, —CH₂CH₃, —CH(CH₃)₂, and so forth. In one embodiment, R⁴ is —C₃₋₆cycloalkyl, examples of which include cyclopropyl.

In one embodiment, R⁴ is —NR⁷R⁸. The R⁷ and R⁸ moieties are independently selected from hydrogen and —C₁₋₆ alkyl, and exemplary R⁷ and R⁸ moieties include hydrogen and —CH₃. Therefore, exemplary R⁴ moieties include —NH₂, —NH(CH₃), and —N(CH₃)₂. In one embodiment, R⁴ is —CH₂SO₂—C₁₋₆alkyl, examples of which include —CH₂SO₂—CH₃.

In one embodiment, R⁴ is pyrazole optionally substituted with —CH₃, examples of which include:

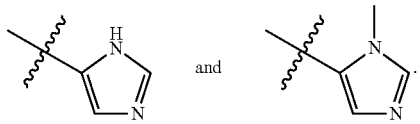

In one embodiment, R⁴ is triazole, examples of which include:

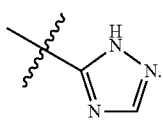

In one embodiment, R⁴ is morpholine, examples of which include:

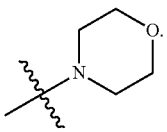 [SMILES: *N1CCOCC1]

In one embodiment, R⁴ is benzoxadiazole, examples of which include:

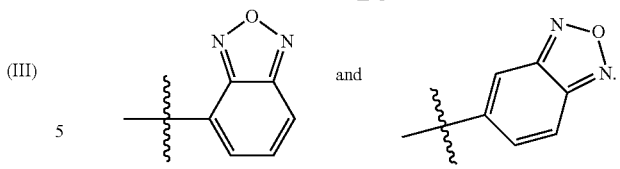

In one embodiment, R⁴ is phenyl optionally substituted with R⁹. The R⁹ moiety is selected from —CN, —COOH, —NO₂, —C₀₋₂alkylene-O—C₁₋₆alkyl, —C(O)NR⁷R⁸; —NR⁷C(O)—C₁₋₆alkyl; —SO₂—C₁₋₆alkyl, —SO₂—NR⁷R⁸, and a nitrogen-containing heteroaryl optionally substituted with 1 or 2-CH₃ groups.

In one embodiment, R⁴ is phenyl. In one embodiment, R⁴ is phenyl substituted with —CN, —COOH, or —NO₂; for example at the 4-position. In one embodiment, R⁴ is phenyl substituted with —C₀₋₂alkylene-O—C₁₋₆alkyl such as —OCH₃ and —(CH₂)₂OCH₃, for example at the 4-position.

In one embodiment, R⁴ is phenyl substituted with —C(O)NR⁷R⁸ or —NR⁷C(O)—C₁₋₆alkyl, for example at the 3 position. The R⁷ and R⁸ moieties are independently selected from hydrogen and —C₁₋₆alkyl, and exemplary R⁷ and R⁸ moieties include hydrogen and —CH₃. Therefore, exemplary R⁴ moieties include phenyl substituted with —C(O)NHCH₃ or —NHC(O)CH₃.

In one embodiment, R⁴ is phenyl substituted with —SO₂—C₁₋₆alkyl, for example —SO₂—CH₃ at the 2, 3 or 4 position. In another embodiment, R⁴ is phenyl substituted with —SO₂—NR⁷R⁸, for example at the 3 position. The R⁷ and R⁸ moieties are independently selected from hydrogen and —C₁₋₆alkyl, and exemplary R⁷ and R⁸ moieties include hydrogen and —CH₃. Therefore, exemplary R⁴ moieties include phenyl substituted with. —SO₂—NH₂ and —SO₂—NHCH₃.

In one embodiment, R⁴ is phenyl substituted with a nitrogen-containing heteroaryl optionally substituted with 1 or 2-CH₃ groups, for example, oxazole, pyrimidine, tetrazole, pyrazole, and pyrazole substituted with two methyl groups. Therefore, exemplary R⁴ moieties include:

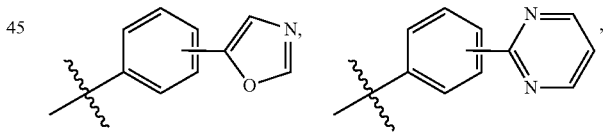

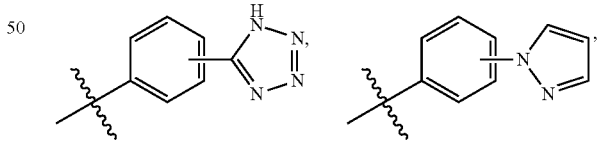

and

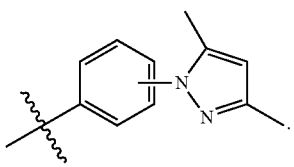

In yet another embodiment, R⁴ is selected from —CH₃; —CH₂CH₃; —CH(CH₃)₂; cyclopropyl; —NH₂; —NH (CH₃); —N(CH₃)₂; —CH₂SO₂—CH₃; pyrazole; pyrazole substituted with —CH₃; triazole; morpholine; benzoxadiazole; and phenyl optionally substituted with $R^9$; where $R^9$ is selected from —CN, —COOH, —NO$_2$, —OCH$_3$, —C(O)NHCH$_3$, —NHC(O)CH$_3$, —SO$_2$—CH$_3$, —SO$_2$—NH$_2$, —SO$_2$—NHCH$_3$, oxazole, pyrimidine, tetrazole, pyrazole, and pyrazole substituted with two methyl groups.

One specific embodiment is formula IIIa:

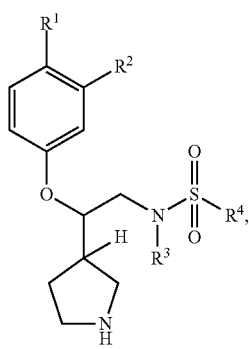

(IIIa)

where $R^1$, $R^2$, $R^3$, and $R^4$ are as defined for formula I. In one exemplary embodiment, $R^1$ and $R^2$ are as defined for formula I; $R^3$ is selected from hydrogen, —CH$_3$, and —C(O)CH$_3$; and $R^4$ is selected from —CH$_3$; —CH$_2$CH$_3$; —CH(CH$_3$)$_2$; cyclopropyl; —NH$_2$; —NH(CH$_3$); —N(CH$_3$)$_2$; —CH$_2$SO$_2$—CH$_3$; pyrazole; pyrazole substituted with —CH$_3$; triazole; morpholine; benzoxadiazole; and phenyl optionally substituted with $R^9$; where $R^9$ is selected from —CN, —COOH, —NO$_2$, —OCH$_3$, —C(O)NHCH$_3$, —NHC(O)CH$_3$, —SO$_2$—CH$_3$, —SO$_2$—NH$_2$, —SO$_2$—NHCH$_3$, oxazole, pyrimidine, tetrazole, pyrazole, and pyrazole substituted with two methyl groups.

In another particular embodiment, Q is —SO$_2$NR$^5$R$^6$, which can be depicted as formula IV:

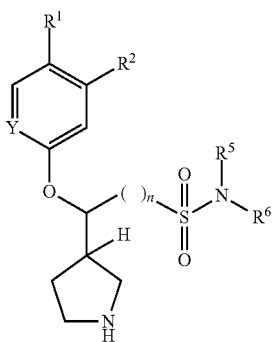

(IV)

The $R^5$ moiety is selected from hydrogen and —C$_{1-6}$alkyl. In one embodiment, $R^5$ is hydrogen. In another embodiment, $R^5$ is —C$_{1-6}$alkyl, examples of which include —CH$_3$, —CH$_2$CH$_3$, and so forth. In still another embodiment, $R^5$ is selected from hydrogen and —CH$_3$.

The $R^6$ moiety is selected from hydrogen, —C$_{1-6}$alkyl, and benzyl. In one embodiment, $R^6$ is hydrogen. In another embodiment, $R^6$ is —C$_{1-6}$alkyl, examples of which include —CH$_3$, —CH$_2$CH$_3$, and so forth. In another embodiment, $R^6$ is benzyl. In still another embodiment, $R^6$ is selected from hydrogen, —CH$_3$, and benzyl.

One specific embodiment is formula IVa:

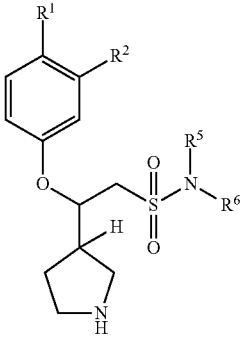

(IVa)

where $R^1$, $R^2$, $R^5$, and $R^6$ are as defined for formula I. In one exemplary embodiment, $R^1$ and $R^2$ are as defined for formula I; $R^5$ is selected from hydrogen and —CH$_3$; and $R^6$ is selected from hydrogen, —CH$_3$, and benzyl.

In addition, particular compounds of formula I that are of interest include those set forth in the Examples below, as well as a pharmaceutically acceptable salt thereof.

General Synthetic Procedures

Compounds of the invention can be prepared from readily available starting materials using the following general methods, the procedures set forth in the Examples, or by using other methods, reagents, and starting materials that are known to those skilled in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (i.e., reaction temperatures, times, mole ratios of reactants, solvents, pressures, etc.) are given, other process conditions can also be used unless otherwise stated. While optimum reaction conditions will typically vary depending on various reaction parameters such as the particular reactants, solvents, and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well known in the art. Protecting groups other than those illustrated in the procedures described herein may be used, if desired. For example, numerous protecting groups, and their introduction and removal, are described in Greene and Wuts, *Protecting Groups in Organic Synthesis*, Fourth Edition, Wiley, New York, 2006, and references cited therein.

More particularly, in the schemes below, P represents an "amino-protecting group," a term used herein to mean a protecting group suitable for preventing undesired reactions at an amino group. Representative amino-protecting groups include, but are not limited to, t-butoxycarbonyl (BOC), trityl (Tr), benzyloxycarbonyl (Cbz), 9-fluorenylmethoxycarbonyl (Fmoc), formyl, benzyl, and the like. Standard deprotection techniques and reagents such as TFA in DCM or HCl in 1,4-dioxane, methanol, or ethanol, are used to remove protecting groups, when present. For example, a BOC group can be removed using an acidic reagent such as hydrochloric acid, trifluoroacetic acid and the like; while a Cbz group can be removed by employing catalytic hydrogenation conditions such as $H_2$ (1 atm), 10% Pd/C in an alcoholic solvent.

Suitable inert diluents or solvents for use in these schemes include, by way of illustration and not limitation, tetrahydrofuran (THF), acetonitrile, N,N-dimethylformamide (DMF), dimethylsulfoxide (DMSO), toluene, dichloromethane (DCM), chloroform ($CHCl_3$), and the like.

All reactions are typically conducted at a temperature within the range of about −78° C. to 110° C., for example at room temperature. Reactions may be monitored by use of thin layer chromatography (TLC), high performance liquid chromatography (HPLC), and/or LCMS until completion. Reactions may be complete in minutes, may take hours, typically from 1-2 hours and up to 48 hours, or days, such as up to 3-4 days. Upon completion, the resulting mixture or reaction product may be further treated in order to obtain the desired product. For example, the resulting mixture or reaction product may be subjected to one or more of the following procedures: dilution (for example with saturated $NaHCO_3$); extraction (for example, with ethyl acetate, $CHCl_3$, DCM, aqueous HCl); washing (for example, with DCM, saturated aqueous NaCl, or saturated aqueous $NaHCO_3$); drying (for example, over $MgSO_4$ or $Na_2SO_4$, or in vacuo); filtration; being concentrated (for example, in vacuo); being redissolved (for example in a 1:1 acetic acid:$H_2O$ solution); and/or purification (for example by preparative HPLC or reverse phase preparative HPLC).

By way of illustration, compounds of formula I, as well as their salts, can be prepared by the following schemes, as well as by the procedures set forth in the examples. In some instances, the * and ** chiral centers of the protected epoxide and protected alcohol were inferred, based on the hydrolytic kinetic resolution step. Alternately, the assignment of the stereochemistry can be accomplished utilizing the established Mosher ester analysis of the intermediate alcohol (see, for example, Dale and Mosher (1969) *J. Org. Chem.* 34(9): 2543-2549).

While the following schemes may illustrate formation of one particular stereoisomer, the other stereoisomers can be made in a similar manner by using a starting material having the appropriate stereochemistry. Similarly, while the following schemes may illustrate carrying forward a mixture of diastereoisomers, the mixture may be separated so that only one stereoisomer is carried forward.

Compounds of formula III (formula I where Q is —$NR^3SO_2R^4$) can be prepared as described in Scheme I:

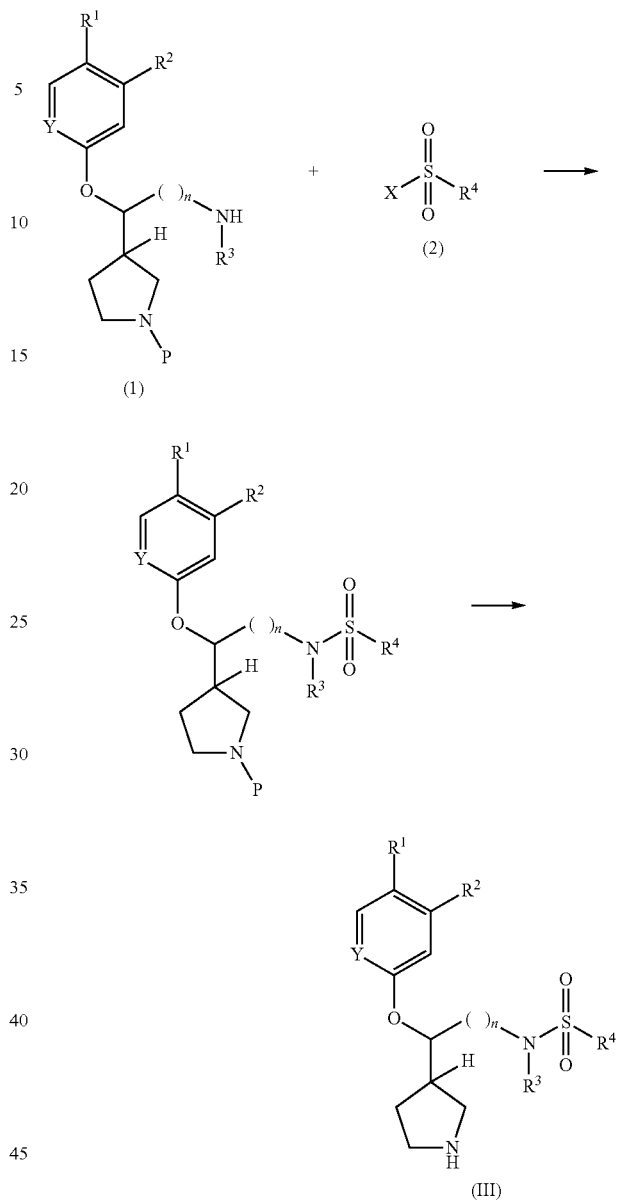

Scheme I

Compounds of formula III can be prepared by reacting the nucleophile 1 with the appropriate sulfonyl halide 2 (where X is a halogen atom) or sulfonic anhydride or sulfamoyl to yield the protected sulfonamide. This reaction is typically conducted at room temperature in a suitable solvent, such as DCM, in the presence of a suitable base, such as diisopropylethylamine or triethylamine. The protected intermediate is then deprotected to yield the desired compound of formula III. Compound 2 is generally commercially available or can be prepared using procedures that are known in the art.

Compound 1

Compound 1 where $R^3$ is —$C_{1-6}$alkyl or —$C(O)C_{1-6}$alkyl can be prepared as follows (illustrated for n=1).

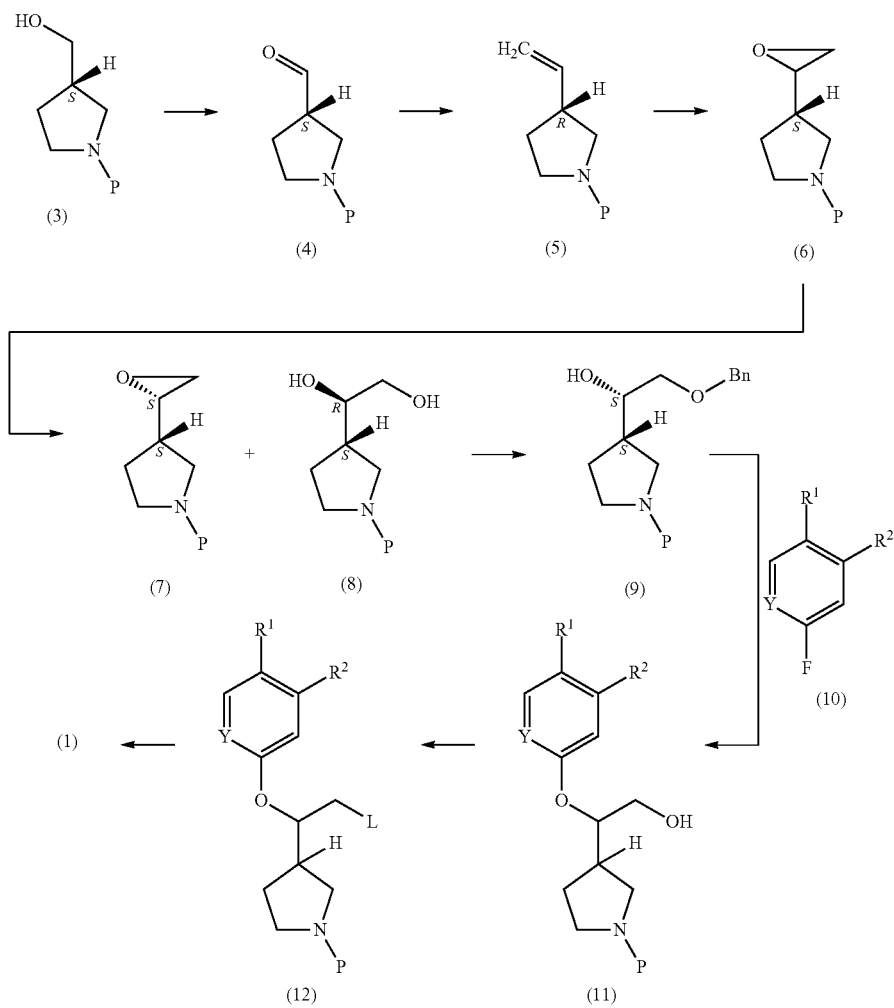

The aldehyde 4 can be prepared by the 2,2,6,6-tetramethyl-1-piperidinyloxy, free radical (TEMPO) mediated oxidation of the alcohol 3. The alcohol 3, where P is Boc or benzyl, is commercially available. Alternately, the aldehyde 4 can be prepared by oxidizing the alcohol 3 using any oxidizing agent suitable for converting a primary alcohol into an aldehyde. Representative oxidizing agents include, for example, dimethyl sulfoxide, Collin's reagent, Corey's reagent, pyridinium dichromate, and the like.

Olefination of the aldehyde 4 by a Wittig reaction yields the alkene 5. Exemplary Wittig reagents include methyltriphenylphosphonium bromide. This step is followed by epoxidation of the alkene using an oxygen transfer catalyst such as methyltrioxorhenium (VII) and hydrogen peroxide as the terminal oxidant to form compound 6.

Compound 6 is then subjected to hydrolytic kinetic resolution to form compounds 7 and 8, which are then separated to provide the epoxide 7 as a single isomer. The next step involves opening the epoxide 7 using a nucleophilic substitution reaction with benzyl alcohol and lithium hydride (LiH) or sodium hydride (NaH) to form compound 9. The alcohol 9 is first coupled with the appropriate aryl fluoride 10 using a nucleophilic aromatic substitution reaction ($S_N Ar$), followed by deprotection of the benzyl group, to yield compound 11. The $S_N Ar$ reaction is typically conducted using LiH or NaH in a solvent such as DMF.

The hydroxyl group of compound 11 is converted into a leaving group, L to form compound 12. For example, compound 11 can undergo tosylation with an appropriate reagent such as p-toluenesulfonyl chloride (TsCl) or tosic anhydride in a suitable base such as triethylenediamine, to form the tosylate ester (compound 12, where L=-$OSO_2$-phenyl-$CH_3$). See, for example, Hartung et al. (1997) Synthesis 12:1433-1438. This step is followed by the addition of a suitably protected primary amine (for example, N-methyltrifluoroacetamide, for $R^3$=methyl) and LiH in a suitable solvent such as DMF to form compound 1 (secondary amine).

Compound 8, once separated, can be converted to the corresponding epoxide by adding chlorotrimethylsilane to a solution of Compound 8 and trimethylorthoacetate in an appropriate solvent such as dichloromethane:

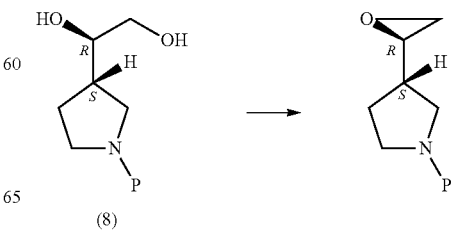

Compound 1 where $R^3$ is hydrogen can be prepared as follows (illustrated for n=1).

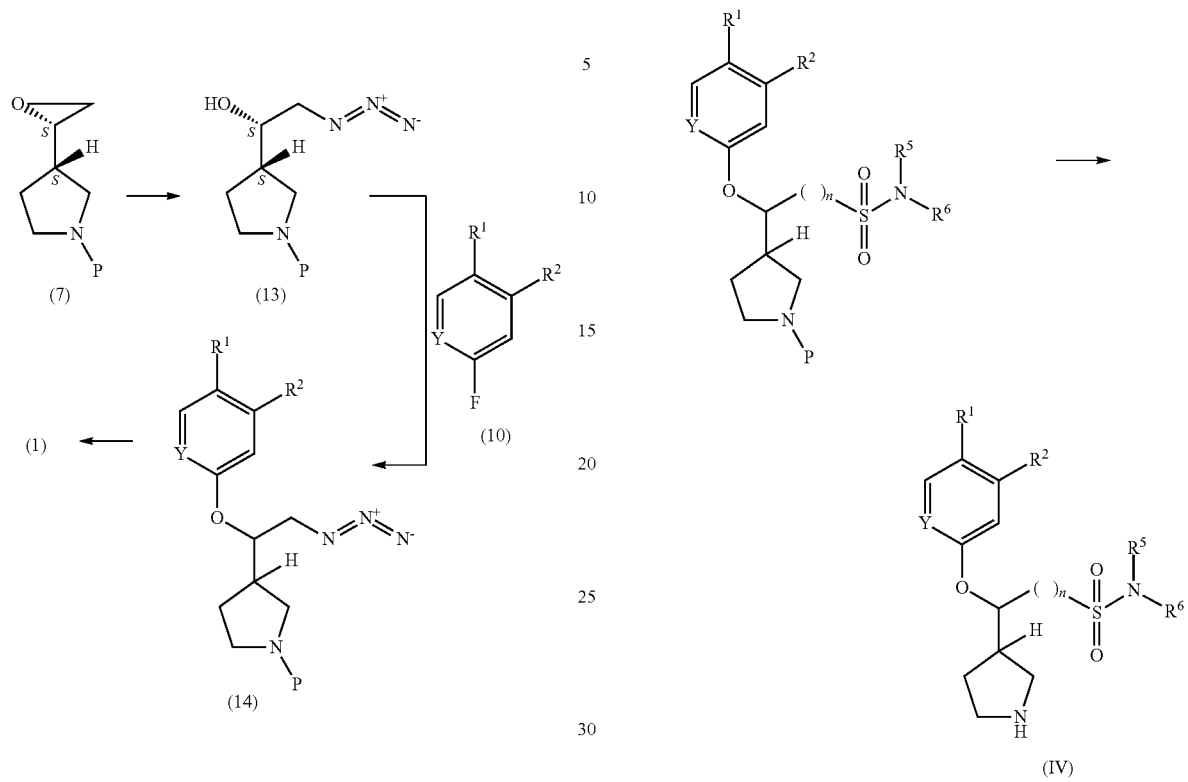

Compounds 7 and 8 are prepared and separated as described above to provide the epoxide 7 as a single isomer. The next step involves an azide addition reaction using sodium azide to form compound 13. The azide 13 is then coupled with the appropriate aryl fluoride 10 using a nucleophilic aromatic substitution reaction ($S_NAr$) to yield compound 14. This reaction is typically conducted using LiH or NaH in a solvent such as DMF. The azide 14 is then reduced by a hydrogenation reaction with a catalyst such as palladium on carbon to yield compound 1 (primary amine).

Compounds of formula IV (formula I where Q is $-SO_2NR^5R^6$) can be prepared as described in Scheme II:

Compounds of formula IV can be prepared by reacting the sulfonyl halide 15 (where X is a halogen atom) with the appropriate amine 16 to yield the protected sulfonamide. This reaction is typically conducted at room temperature in a suitable solvent, such as DCM. The protected intermediate is then deprotected to yield the desired compound of formula IV. Compound 16 is generally commercially available or can be prepared using procedures that are known in the art.

Compound 15

Compound 15 can be prepared as follows.

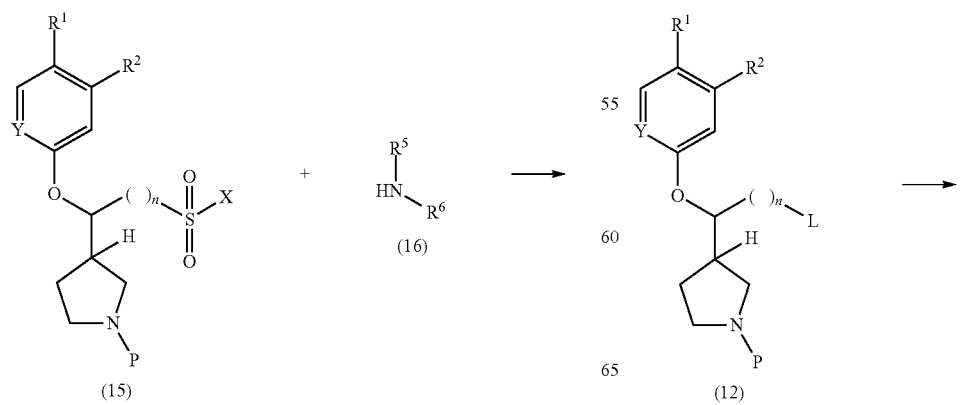

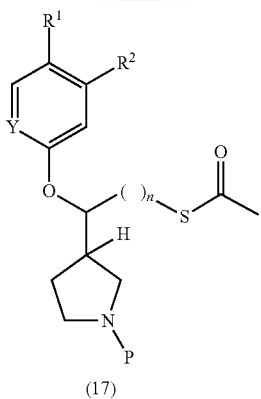

(17)

Compound 12 (for example, where L=-OSO$_2$-phenyl-CH$_3$) is reacted with potassium thioacetate in a suitable solvent such as ethanol, to yield compound 17. This step is followed by an oxidation reaction using an N-halosuccinimide such as N-chlorosuccinimide or N-bromosuccinimide in dilute HCl to form compound 15 (where X is chloro or bromo, respectively). See, for example, Nishiguchi et al., (2006) *Synthesis* 24:4131-4134.

If desired, pharmaceutically acceptable salts of the compounds of formula I can be prepared by contacting the free acid or base form of a compound of formula I with a pharmaceutically acceptable base or acid.

Certain of the intermediates described herein are believed to be novel and accordingly, such compounds are provided as further aspects of the invention including, for example, compounds of formulas e, f, g, and h:

(e)

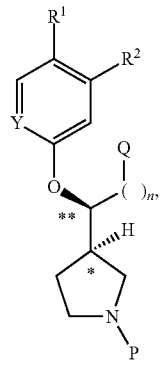

(f)

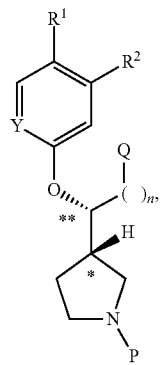

(g)

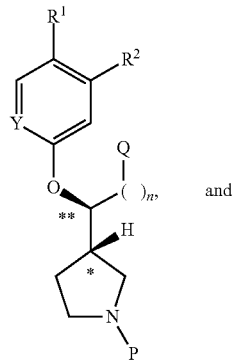 and (h)

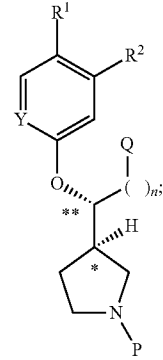

where Y, R$^1$, R$^2$, n, and Q are as defined for formula I; and P represents an amino-protecting group, particularly t-butoxycarbonyl (BOC). In one embodiment of the invention, compounds of the invention can be prepared by deprotecting a compound of formula II:

(II)

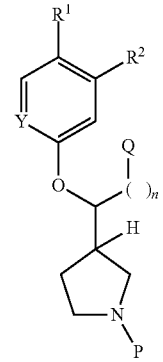

where Y, R$^1$, R$^2$, n, and Q are as defined for formula I, and P represents an amino-protecting group, to provide a compound of formula I, or a salt thereof. In one particular embodiment, such protected compounds have the formulas e, f, g, or h.

Further details regarding specific reaction conditions and other procedures for preparing representative compounds of the invention or intermediates thereof are described in the Examples set forth herein.

Utility

Compounds of the invention possess serotonin reuptake inhibitory activity, and in one embodiment, at nanomolar potencies. Thus, these compounds have therapeutic utility as serotonin reuptake inhibitors. In one embodiment, the compounds of the invention act primarily as serotonin reuptake inhibitors, and thus exhibit only minimal or sub-therapeutic activity as norepinephrine reuptake inhibitors and/or dopamine reuptake inhibitors.

The inhibition constant ($K_i$) of a compound is the concentration of ligand in a radioligand binding inhibition assay that would occupy 50% of the transporters if no radioligand were present. $K_i$ values can be determined from radioligand binding studies with $^3$H-citalopram as described in Assay 1. These $K_i$ values are derived from $IC_{50}$ values in the binding assay using the Cheng-Prusoff equation and the $K_d$ of the radioligand (Cheng & Prusoff (1973) *Biochem. Pharmacol.* 22(23): 3099-3108). Functional $IC_{50}$ values can be determined in the functional inhibition of uptake assays described in Assay 2. These $IC_{50}$ values can be converted to $K_i$ values using the Cheng-Prusoff equation and the $K_m$ of the transmitter for the transporter. It is noted however, that the uptake assay conditions described in Assay 2 are such that the $IC_{50}$ values are very close to the $K_i$ values, should a mathematical conversion be desired, since the 5-HT concentration used in the assay is well below its $K_m$ for the transporter.

One measure of the affinity of a compound for SERT is the inhibitory constant ($pK_i$) for binding to the transporter. The $pK_i$ value is the negative logarithm to base 10 of the $K_i$. Compounds of the invention of particular interest are those having a $pK_i$ at SERT greater than or equal to 5.0, particularly those having a $pK_i$ at SERT greater than or equal to 7.0, and even more particularly those having a $pK_i$ at SERT greater than or equal to 8.0. Another measure of serotonin reuptake inhibition is the $pIC_{50}$ value. In one embodiment, compounds of interest are those having a serotonin reuptake inhibition $pIC_{50}$ value greater than or equal to 5.0, particularly those having a $pIC_{50}$ value greater than or equal to 7.0, and even more particularly those having a $pIC_{50}$ value greater than or equal to 8.0. Such values can be determined by techniques that are well known in the art, as well as in the assays described herein.

It is noted that in some cases, compounds of the invention may possess weak serotonin reuptake inhibitory activity. In such cases, those of ordinary skill in the art will recognize that those compounds still have utility as research tools.

Exemplary assays to determine the serotonin reuptake inhibiting activity of compounds of the invention include by way of illustration and not limitation, assays that measure SERT binding, for example, as described in Assay 1 and in Tsuruda et al. (2010) *Journal of Pharmacological and Toxicological Methods* 61(2): 192-204. Useful secondary assays include neurotransmitter uptake assays to measure inhibition of serotonin uptake into cells expressing the human or rat recombinant transporter as described in Assay 2, and ex vivo radioligand binding assays that are used to determine the in vivo occupancy of SERT in tissue as described in Assay 3. Other assays that are useful to evaluate pharmacological properties of test compounds include, but are not limited to, cold ligand binding kinetics assays (Motulsky and Mahan (1984) *Molecular Pharmacol.* 25(1): 1-9) with membranes prepared from cells expressing hSERT conventional membrane radioligand binding assays using radiolabeled, for example, tritiated, test compound; radioligand binding assays using native tissue from, for example rodent or human brain; neurotransmitter uptake assays using human or rodent platelets; and neurotransmitter uptake assays using crude, or pure, synaptosome preparations from rodent brain.

Exemplary in vivo assays include the rat peripheral serotonin model described, for example, in Ortiz et al. (1992) *British Journal of Pharmacology* 105:941-946; and the rat serotonin syndrome model described, for example, in Izumi et al. (2006) *European Journal of Pharmacology* 532:258-264. The rat monocrotaline model of pulmonary arterial hypertension is described, for example, in Kato et al. (2008) *J. Cardiovasc. Pharmacol.* 51(1):18-23, which is a reliable predictor of clinical efficacy for the treatment of pulmonary arterial hypertension. Platelet aggregation assays are described for example, in Carneiro et al. (2008) *J. Clin. Invest.* 118(4):1544-1552. Thrombosis can be measured by several models, including the arterial thrombosis rodent model described, in Krekora et al. (1999) *Thrombosis Research* 96:407-414, and the rodent model of microarterial anastomosis, described in Nayak et al (2005) *Arch Otolaryngol Head Meck Surg.* 131:800-803). The mouse hypoxia model is also useful to evaluate the compounds of the invention, and is described for example, in Marcos et al., (2003) *Am. J. Respir. Crit. Care Med.* 168:487-493. The aforementioned assays are useful in determining the therapeutic utility. Other properties and utilities of compounds of the invention can be demonstrated using various in vitro and in vivo assays well known to those skilled in the art.

In one embodiment, the compounds of the invention are peripherally selective such that they exist predominantly in the periphery (e.g., plasma) as compared to the central nervous system (e.g., the brain or cerebrospinal fluid), as measured in animal models. One method of evaluating peripherally selectivity is to determine the ratio of the free plasma concentration as compared to the free brain or cerebrospinal fluid concentration, measured by the AUC, which is the integral of the drug concentration after it is administered. In one embodiment, compounds of the invention exhibit a ratio of free plasma concentration:free brain concentration greater than 10. One exemplary assay to measure AUC values is described in Assay 4. Another method of evaluating peripherally selectivity is to measure the level of SERT inhibition in plasma as compared to the level of SERT inhibition in the brain. In one embodiment, compounds of the invention exhibit a ratio of plasma:brain SERT inhibition in the range of about 20:1 to about 80:1 (measured in rats).

Compounds of the invention are expected to be useful for the treatment and/or prevention of medical conditions in which the regulation of peripheral monoamine transporter function is implicated, in particular those conditions mediated by or responsive to the inhibition of serotonin reuptake. Thus, it is expected that patients suffering from a disease or disorder that is treated by the inhibition of the serotonin transporter can be treated by administering a therapeutically effective amount of a serotonin reuptake inhibitor of the invention.

The amount of active agent administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the active agent and any secondary agents being administered, and the like. Treatment of a patient suffering from a disease or medical condition (such as pulmonary arterial hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. Indicators for the diseases and conditions described herein, are well known to those skilled in the art, and are readily available to the treating physician. Continuous monitoring by the physician will ensure that the optimal amount of active agent will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Pulmonary Arterial Hypertension (PAH)

Compounds having serotonin reuptake inhibiting activity have been shown to prevent or reverse PAH in animal models. See, for example, Zhu et al. (2009) *Clinical and Experimental Pharmacology and Physiology* 36(8): e1-e5 and Shah et al. (2009) *Chest* 136(3):694-700. Thus, compounds of the invention are expected to find utility in treating PAH, as well as potentially finding utility in preventing disease progression. In addition, compounds of the invention are expected to find utility in treating PAH associated with chronic obstructive pulmonary disease (COPD); see, for example, Chaouat et al. (2009) *Chest* 136:3. For treatment of PAH, the therapeutically effective amount is typically the amount that is sufficient to lower the pulmonary vascular resistance. Other goals of therapy are to improve a patient's exercise capacity and to decrease mortality associated with PAH. For example, in a clinical setting, the therapeutically effective amount can be the amount that improves a patient's ability to walk comfortably for a period of 6 minutes (covering a distance of approximately 20-40 meters). When used for treating this disorder, compounds of the invention may be administered with secondary agents, including by way of illustration and not limitation, α-adrenergic antagonists, $\beta_1$-adrenergic receptor antagonists, $\beta_2$-adrenergic receptor agonists, angiotensin-converting enzyme inhibitors, anticoagulants, calcium channel blockers, diuretics, endothelin receptor antagonists, PDE-5 inhibitors, prostaglandin analogs, and combinations thereof.

Thrombosis-Induced Cardiovascular Diseases

Serotonin has been found to play a role in platelet activation (See, for example, Walther et al. (2003) *Cell* 115:851-862). Thus, since the compounds of the invention have serotonin reuptake inhibiting activity, they are expected to find utility in anti-platelet therapy, in particular for treatment of: thrombosis-induced cardiovascular diseases such as: atherosclerosis; cerebrovascular diseases such as stroke; congestive heart failure; coronary artery disease such as angina; myocardial infarction (heart attack) and other forms of ischemic heart disease; metabolic syndrome (Syndrome X); peripheral vascular disease; pulmonary embolism; thrombosis, including peripheral vascular thrombosis; and thrombotic re-occlusion that may occur after surgery. When used for treating such disorders, compounds of the invention may be administered in combination with one or more other anti-thrombotic agents.

Gastrointestinal Disorders

It has been found that abnormalities in serotonin reuptake can alter enteric serotonergic signaling, leading to sensory, motor, and secretory gut dysfunctions. See, for example, Colucci et al. (2008) *Trends in Molecular Medicine* 14(7): 295-304. Thus, compounds of the invention are expected to find utility in treating gastrointestinal disorders in the mid or lower gastrointestinal tract. These include, for example, irritable bowel syndrome, diarrhea-predominant irritable bowel syndrome, dyspepsia, functional abdominal bloating, functional constipation, and functional diarrhea. When used for treating gastrointestinal disorders, compounds of the invention may be administered with secondary agents, including by way of illustration and not limitation, anti-diarrheals, antispasmodic agents (e.g., anticholinergics and smooth muscle relaxants), and combinations thereof.

Cancer

Recent studies have indicated that the serotonin neurotransmitter transporter plays a role in cancer. See, for example, Gil-Ad et al (2008) *International Journal of Oncology* 33:277-286 and Amit et al. *European Neuropsychopharmacology* (2009) 19:726-734. Thus, compounds of the invention are expected to find utility as anti-proliferative agents in treating cancer such as colorectal cancer and leukemia, and may be administered with secondary agents such as anti-neoplastic agents, anti-proliferative agents, cytotoxic agents, tumor growth inhibitors, and combinations thereof.

Rheumatoid Arthritis

Compounds having serotonin reuptake inhibiting activity have been shown to exhibit anti-inflammatory properties (Roumestan et al. *Respiratory Research* (2007) 8:35), more particularly in a rheumatoid arthritis animal model (Sacre et al. (2010) *Arthritis & Rheumatism* 62(3):683-693. Thus, compounds of the invention are expected to find utility in the treatment of rheumatoid arthritis, and may be administered with secondary agents such as corticosteroids; disease modifying anti-rheumatic drugs including hydroxychloroquine, leflunomide, methotrexate, sulfasalazine, gold salts such as intramuscular gold, interleukin-1 receptor antagonist therapies such as anakinra, B cell depleting agents such as rituximab, T-cell costimulatory blocking agents such as abatacept, tumor necrosis factor inhibitors such as adalimumab, etanercept, and infliximab, and immunomodulatory and cytotoxic agents such as azathioprine, cyclophosphamide, and cyclosporine A; non-steroidal anti-inflammatory agents; and combinations thereof.

Osteoarthritis

The serotonin reuptake inhibitor, duloxetine, has been shown to be useful in reducing pain severity in patients with osteoarthritis pain of the knee. Thus, compounds of the invention are also expected to find utility in the treatment of osteoarthritis, and may be administered with secondary agents such as analgesics (e.g., acetaminophen), corticosteroids, non-steroidal anti-inflammatory agents; and combinations thereof.

Osteoporosis

Gut-derived serotonin inhibits bone formation. Recent studies have explored whether affecting the biosynthesis of gut-derived serotonin could treat osteoporosis by increasing bone formation, and concluded that inhibiting such biosynthesis could become a new treatment for osteoporosis (Yadav et al. *Nature Medicine* (2010) 16:308-312). Thus, compounds of the invention are also expected to find utility in the treatment of osteoporosis.

Diabetes

The selective serotonin reuptake inhibitor, s-citalopram, has been shown to be useful in treating patients with co-morbid major depression and diabetes mellitus, showing a potential ability to improve glycemic control (Amsterdam et al. (2006) *Neuropsychobiology* 54:208-214). Studies with the selective serotonin reuptake inhibitor, fluvoxamine, suggest that such compounds may find utility in reducing postprandial hyperglycemia (Moore et al. (2005) *Am. J. Physiol. Endocrinol. Metab.* 288:E556-E563). Thus, compounds of the invention are also expected to find utility in the treatment of diabetes, and may be administered with orally effective antibiotic secondary agents such as: biguanides such as metformin; glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

Research Tools

Since compounds of the invention possess serotonin reuptake inhibition activity, they are also useful as research tools for investigating or studying biological systems or samples having serotonin transporters. Any suitable biological system or sample having serotonin transporters may be employed in such studies, which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, serotonin reuptake in a mammal is inhibited by administering a serotonin reuptake-inhibiting amount of a compound of the invention. Compounds of the invention can also be used as research tools by conducting biological assays using such compounds.

When used as a research tool, a biological system or sample comprising a serotonin transporter is typically contacted with a serotonin reuptake-inhibiting amount of a compound of the invention. After the biological system or sample is exposed to the compound, the effects of inhibiting serotonin reuptake are determined using conventional procedures and equipment. Exposure encompasses contacting cells or tissue with the compound, administering the compound to a mammal, for example by i.p. or i.v. administration, by the use of an implantable pump such as the Alzet® osmotic pump, and so forth. This determining step may comprise measuring a response, i.e., a quantitative analysis or may comprise an observation, i.e., a qualitative analysis. Measuring a response involves, for example, determining the effects of the compound on the biological system or sample using conventional procedures and equipment, such as a serotonin reuptake assay. The assay results can be used to determine the activity level as well as the amount of compound necessary to achieve the desired result, i.e., a serotonin reuptake-inhibiting amount.

Additionally, compounds of the invention can be used as research tools for evaluating other chemical compounds, and thus are useful in screening assays to discover, for example, new compounds having serotonin reuptake-inhibiting activity. In this manner, a compound of the invention is used as a standard in an assay to allow comparison of the results obtained with a test compound and with compounds of the invention to identify those test compounds that have about equal or superior reuptake-inhibiting activity, if any. For example, reuptake data for a test compound or a group of test compounds is compared to the reuptake data for a compound of the invention to identify those test compounds that have the desired properties, e.g., test compounds having reuptake-inhibiting activity about equal or superior to a compound of the invention, if any.

This aspect of the invention includes, as separate embodiments, both the generation of comparison data (using the appropriate assays) and the analysis of the test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include serotonin reuptake assays.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration. Further, the compounds of the invention may be administered, for example orally, in multiple doses per day (e.g. twice, three times or four times daily), in a single daily dose, in a twice-daily dose, in a single weekly dose, and so forth. It will be understood that any form of the compounds of the invention, (i.e., free base, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts and solvates of that compound.

The pharmaceutical compositions of the invention typically contain a therapeutically effective amount of a compound of the invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers, and the like, using conventional procedures and equipment.

In one embodiment, the pharmaceutical compositions are suitable for oral administration. One exemplary dosing regimen would be an oral dosage form administered once or twice daily. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (i.e., as capsules, tablets, pills, and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring, and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methylcellulose acetate succinate, and the like. Examples of pharmaceutically acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions that can be used include polymeric substances and waxes. The active agent can also be in microencapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, i.e., each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, and glycerin. Such compositions are typically prepared by adding chilled or pressurized hydrofluoroalkane to a suitable container containing the active agent, ethanol (if present), and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (e.g., by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. A typical parenteral formulation is a sterile pH 4-7 aqueous solution of the active agent. Parenteral formulations may also contain one or more solubilizers, stabilizers, preservatives, wetting agents, emulsifiers, and dispersing agents.

These formulations may be rendered sterile by use of a sterile injectable medium, a sterilizing agent, filtration, irradiation, or heat.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones, and the like, and incorporated into a patch or similar delivery system. Additional excipients including gelling agents, emulsifiers and buffers, may be used in such transdermal compositions if desired.

Secondary Agents

The compounds of the invention may be useful as the sole treatment of a disease or may be combined with one or more other therapeutic agents in order to obtain the desired therapeutic effect. Thus, in one embodiment, pharmaceutical compositions of the invention contain other drugs that are co-administered with a compound of the invention. For example, the composition may further comprise one or more drugs (also referred to as "secondary agents(s)"). Numerous examples of such therapeutic agents are well known in the art, and examples are described herein. By combining a compound of the invention with a secondary agent, double therapy can be achieved, i.e., serotonin reuptake inhibitory activity and activity associated with the secondary agent. Accordingly, in yet another aspect of the invention, a pharmaceutical composition comprises a compound of the invention, a second active agent, and a pharmaceutically acceptable carrier. Third, fourth etc. active agents may also be included in the composition. In combination therapy, the amount of compound of the invention that is administered, as well as the amount of secondary agents, may be less than the amount typically administered in monotherapy.

A compound of the invention may be either physically mixed with the second active agent to form a composition containing both agents; or each agent may be present in separate and distinct compositions which are administered to the patient simultaneously or sequentially. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent, and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (e.g., one hour later or three hours later). Alternatively, the combination may be administered by different routes of administration, i.e., one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount, i.e., are typically administered in an amount that produces a therapeutically beneficial effect when co-administered with a compound of the invention. The secondary agent can be in the form of a pharmaceutically acceptable salt, solvate, optically pure stereoisomer, and so forth. Thus, secondary agents listed below are intended to include all such forms, and are commercially available or can be prepared using conventional procedures and reagents.

In one embodiment, compounds of the invention are administered in combination with an α-adrenergic antagonist, representative examples of which include, but are not limited to, doxazosin, prazosin, tamsulosin, and terazosin.

Compounds of the invention may also be administered in combination with a $\beta_1$-adrenergic receptor antagonist ("$\beta_1$-blockers"). Representative $\beta_1$-blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$-antagonist is selected from atenolol, bisoprolol, metoprolol, propranolol, sotalol, and combinations thereof. Typically, the $\beta_1$-blocker will be administered in an amount sufficient to provide from about 2-900 mg per dose.

In one embodiment, compounds of the invention are administered in combination with a $\beta_2$-adrenergic receptor agonist, representative examples of which include, but are not limited to, albuterol, bitolterol, fenoterol, formoterol, indacaterol, isoetharine, levalbuterol, metaproterenol, pirbuterol, salbutamol, salmefamol, salmeterol, terbutaline, and the like. Typically, the $\beta_2$-adrenoreceptor agonist will be administered in an amount sufficient to provide from about 0.05-500 µg per dose.

Compounds of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltopril, pentopril, perindopril, quinapril, quinaprilat, ramipril, ramiprilat, saralasin acetate, spirapril, temocapril, trandolapril, zofenopril, and combinations thereof. In a particular embodiment, the ACE inhibitor is selected from: benazepril, enalapril, lisinopril, ramipril, and combinations thereof.

In one embodiment, a compound of the invention is administered in combination with an anticoagulant, representative examples of which include, but are not limited to: coumarines such as warfarin; heparin; and direct thrombin inhibitors such as argatroban, bivalirudin, dabigatran, and lepirudin.

In another embodiment, compounds of the invention are administered in combination with an anti-thrombotic agent. Representative anti-thrombotic agents include, but are not limited to, aspirin, anti-platelet agents, heparin, and combinations thereof. Anti-platelet agents include: adenosine diphosphate receptor inhibitors such as clopidogrel (e.g., clopidogrel bisulfate), prasugrel, and ticlopidine; phosphodiesterase inhibitors such as cilostazol; glycoprotein IIB/IIIA inhibitors, typically administered intravenously, such as abciximab, defibrotide, eptifibatide, and tirofiban; and adenosine reuptake inhibitors such as dipyridamole. Exemplary combination anti-thrombotic agents include aspirin combined with dipyridamole.

In one embodiment, compounds of the invention are administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexyline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof. Typically, the calcium channel blocker will be administered in an amount sufficient to provide from about 2-500 mg per dose.

In one embodiment, compounds of the invention are administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosernide, bumetanide, butazolamide, chloraminophenamide, clofenamide, clopamide, clorexolone, disulfamide, ethoxolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg, or 25 mg per day.

In a particular embodiment, compounds of the invention are administered in combination with an endothelin receptor antagonist. Representative endothelin receptor antagonists include, but are not limited to, selective endothelin receptor antagonists (e.g., sitaxentan, ambrisentan, atrasentan, BQ-123), which affect endothelin A receptors, and dual endothelin receptor antagonists (e.g., bosentan, tezosentan), which affect both endothelin A and B receptors.

In another embodiment, compounds of the invention are administered in combination with a muscarinic antagonist (i.e., anticholinergic agent). Representative muscarinic antagonists include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like.

In still another embodiment, compounds of the invention are administered in combination with a non-steroidal anti-inflammatory agent (NSAID). Representative non-steroidal anti-inflammatory agents (NSAIDs) include, but are not limited to: acemetacin, acetyl salicylic acid, alclofenac, alminoprofen, amfenac, amiprilose, amoxiprin, anirolac, apazone, aspirin, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, nimesulide, nitroflurbiprofen, olsalazine, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In a particular embodiment, a compound of the invention is administered in combination with a phosphodiesterase-5 (PDE-5) inhibitor. Representative PDE-5 inhibitors include, but are not limited to, avanafil, lodenafil, mirodenafil, sildenafil (Revatio®), tadalafil (Adcirca®), vardenafil (Levitra®), and udenafil.

In another embodiment, compounds of the invention are administered in combination with a prostaglandin analog (also referred to as prostanoids or prostacyclin analogs). Representative prostaglandin analogs include, but are not limited to, beraprost sodium, bimatoprost, epoprostenol, iloprost, latanoprost, travoprost, and treprostinil.

The following formulations illustrate representative pharmaceutical compositions of the present invention:

Exemplary Hard Gelatin Capsules for Oral Administration

A compound of the invention (50 g), spray-dried lactose (440 g) and magnesium stearate (10 g) are thoroughly blended. The resulting composition is then loaded into hard gelatin capsules (500 mg of composition per capsule).

Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Exemplary Gelatin Capsule Formulation for Oral Administration

A compound of the invention (100 mg) is thoroughly blended with polyoxyethylene sorbitan monooleate (50 mg) and starch powder (250 mg). The mixture is then loaded into a gelatin capsule (400 mg of composition per capsule). Alternately, a compound of the invention (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation for Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve.

A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate, and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of compositions per tablet).

Exemplary Suspension Formulation for Oral Administration

The following ingredients are mixed to form a suspension containing 100 mg of active agent per 10 mL of suspension:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5N aqueous hydrochloric acid or 0.5N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 μg to about 500 μg of the compound of the invention per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard meaning:

| | |
|---|---|
| AcOH | acetic acid |
| Boc | t-butoxycarbonyl |
| DCM | dichloromethane (i.e., methylene chloride) |
| DMF | N,N-dimethylformamide |
| DMSO | dimethylsulfoxide |
| EtOAc | ethyl acetate |
| EtOH | ethanol |
| MeCN | acetonitrile |
| MeOH | methanol |
| TEMPO | 2,2,6,6-tetramethyl-1-piperidinyloxy, free radical |
| TFA | trifluoroacetic acid |
| THF | tetrahydrofuran |

Any other abbreviations used herein but not defined have their standard, generally accepted meaning. Unless noted otherwise, all materials, such as reagents, starting materials and solvents, were purchased from commercial suppliers (such as Sigma-Aldrich, Fluka Riedel-de Haën, and the like) and were used without further purification.

Preparation 1

(R)-3-vinylpyrrolidine-1-carboxylic Acid t-Butyl Ester 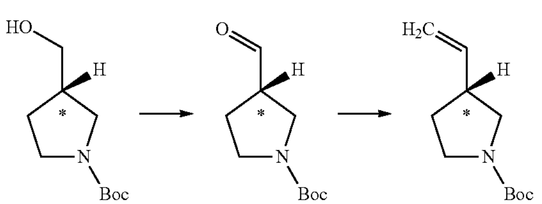 (1a)

A solution of (S)-3-hydroxymethyl-pyrrolidine-1-carboxylic acid t-butyl ester (25.0 g, 124 mmol, 1.0 eq.) in DCM (200 mL) was cooled with stirring to 0° C. A solution of potassium bromide (1.5 g, 12.4 mmol, 0.1 eq.) and sodium bicarbonate (1.5 g, 17.4 mmol, 0.14 eq.) dissolved in water (100 mL) was added. After 15 minutes of stirring at 0° C., TEMPO (195.3 mg, 1.2 mmol, 0.01 eq.) was added, followed by the slow addition of sodium hypochlorite (77.3 mL, 136.6 mmol, 1.1 eq.) dropwise keeping the internal temperature in the 6-8° C. range. The mixture was placed in an ice bath until the layers separated. The organic layer was separated and the aqueous layer was extracted with DCM (200 mL). The combined organic layers were washed with saturated aqueous NaCl (200 mL), dried over $Na_2SO_4$, filtered, and concentrated to yield crude compound 1a (21.5 g).

A slurry of methyltriphenylphosphonium bromide (16.1 g, 45.2 mmol, 3.0 eq.) in THF (50 mL) was cooled to −78° C. 1M Sodium bis(trimethylsilyl)amide in THF (38.0 mL, 41.4 mmol, 2.75 eq.) was added and the mixture was stirred for 30 minutes. A solution of compound 1a (3.0 g, 15.0 mmol, 1.0 eq.) in THF (10 mL) was slowly added and the mixture was stirred at −78° C. for 2 hours. The mixture was warmed to room temperature over 3 hours and the reaction was quenched with half saturated $NH_4Cl$ (50 mL). The organic layer was washed with saturated aqueous NaCl (50 mL). The organic layer was collected, dried over $MgSO_4$, filtered, and concentrated. The resulting oil was slurried in hexanes (50 mL) and the precipitate was filtered off. The filtrate was concentrated, diluted with hexanes (25 mL), and chilled at −20° C. overnight. The precipitate was filtered off and the filtrate was purified by column chromatography (0-100% EtOAc in hexanes) to yield the title compound as an oil (2.1 g).

$^1$H-NMR (400 MHz, DMSO): δ (ppm)=5.81-5.71 (m, 1H), 5.13-5.07 (m, 1H), 5.05-5.01 (m, 1H), 3.56-3.42 (m, 2H), 3.32-3.24 (m, 1H), 3.08-3.0 (m, 1H), 2.83-2.71 (m, 1H), 2.04-1.95 (m, 1H), 1.74-1.60 (m, 1H), 1.45 (s, 9H).

Preparation 2

(S)—(S)-3-Oxiranylpyrrolidine-1-carboxylic Acid t-Butyl Ester and (S)-3-((R)-1,2-Dihydroxyyethyl) pyrrolidine-1-carboxylic Acid t-Butyl Ester 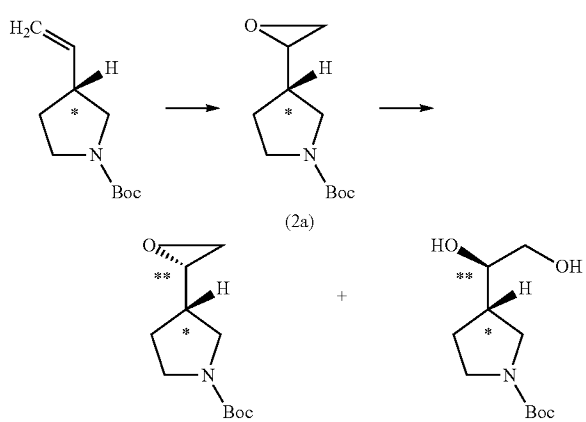 (2a)

To (R)-3-vinylpyrrolidine-1-carboxylic acid t-butyl ester (6.1 g, 30.8 mmol, 1.0 eq.) was added 3-pyridinecarbonitrile (320 mg, 3.1 mmol, 0.1 eq.) and methyltrioxorhenium (VII) (192 mg, 769 mol, 0.025 eq.). The mixture was stirred until homogeneous. 30% Hydrogen peroxide (33:77, hydrogen peroxide:H₂O, 4.08 mL, 40.0 mmol, 1.3 eq.) was added, and the mixture was placed in a ice water bath and stirred for 2 hours. Additional methyltrioxorhenium (VII) (50 mg) was added. The organic layer was collected and washed with a saturated sodium metabisulfite solution under an ice bath. The material was then washed with saturated aqueous NaCl. The organic layer was collected, dried over Na₂SO₄, filtered, and concentrated. The peroxide layer was carefully quenched by adding ice followed by adding saturated sodium metabisulfite solution dropwise at 0° C. The crude product was purified by column chromatography (0-100% EtOAc in hexanes) to give compound 2a as a light yellow oil (4.2 g).

¹H-NMR (400 MHz, DMSO): δ (ppm)=3.38-3.28 (m, 2H), 3.24-3.12 (m, 1H), 3.08-2.98 (m, 1H), 2.94-2.88 (m, 1H), 2.72-2.66 (m, 1H), 2.52-2.46 (m, 1H), 2.28-2.00 (m, 1H), 1.98-1.84 (m, 1H), 1.76-1.60 (m, 1H), 1.40 (s, 9H). (S,S)-(+)-N,N'-Bis(3,5-di-t-butylsalicylidene)-1,2-cyclohexanediaminocobalt (II) (24.1 mg, 39.8 mol) was dissolved in toluene (2.0 mL). AcOH was added (4.5 µL), and the resulting mixture was stirred at room temperature for 1 hour under air. The mixture was then concentrated and dried under vacuum. Compound 2a (1.7 g, 8.0 mmol) was added, followed by water (71.8 µL), and the resulting mixture was stirred vigorously for 6 hours. Hexanes (10 mL) was added. The hexanes layer was then collected. The bottom layer of black oil containing the diol was washed twice with hexanes (10 mL). The hexane washes were combined and allowed to settle at −20° C. overnight. The hexane solution was then decanted and concentrated.

The resulting oil was purified by flash column chromatography (0-100% EtOAc in hexanes) to yield (S)—(S)-3-oxiranylpyrrolidine-1-carboxylic acid t-butyl ester as an oil (750 g): ¹H-NMR (400 MHz, DMSO): δ (ppm)=3.54-3.27 (m, 2H), 3.25-3.11 (m, 1H), 3.11-2.97 (m, 1H), 2.91 (ddd, J=6.6, 4.0, 2.7 Hz, 1H), 2.69 (dd, J=4.8, 4.1 Hz, 1H), 2.55-2.50 (m, 1H), 2.06 (dq, J=14.1, 7.2 Hz, 1H), 1.98-1.84 (m, 1H), 1.78-1.60 (m, 1H), 1.39 (s, 9H).

The black oil containing the diol was dissolved in DCM and purified by flash column chromatography (10-15% MeOH in DCM) to yield (S)-3-((R)-1,2-dihydroxyethyl)pyrrolidine-1-carboxylic acid t-butyl ester as a black oil (0.680 µg): ¹H-NMR (400 MHz, DMSO): δ (ppm)=5.75 (s, 1H), 4.63 (d, J=5.1 Hz, 1H), 4.52 (t, J=5.5 Hz, 1H), 3.43-3.23 (m, 4H), 3.16-3.00 (m, 1H), 2.94 (dt, J=13.4, 10.1 Hz, 1H), 2.17 (qd, J=15.2, 7.3 Hz, 1H), 1.96-1.74 (m, 1H), 1.75-1.54 (m, 1H), 1.38 (s, 9H).

Preparation 3

(S)-3-[(S)-2-Hydroxy-1-(4-trifluoromethylphenoxy)ethyl]pyrrolidine-1-carboxylic Acid t-Butyl Ester

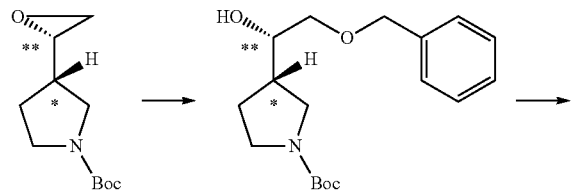

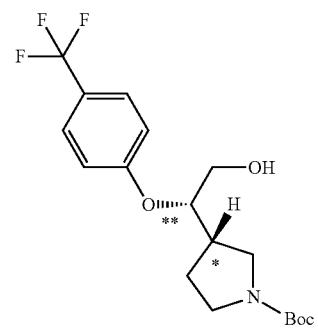

Benzyl alcohol (20 mL) was degassed under nitrogen. NaH (472 mg, 19.7 mmol) was added in small portions, resulting in a cloudy solution, which was heated at 50° C. prior to completion of the NaH addition. (S)—(S)-3-Oxiranylpyrrolidine-1-carboxylic acid t-butyl ester (3.5 g, 16 mmol) was added and the resulting mixture was stirred at 50° C. overnight. The mixture was cooled to 0° C., and the reaction was quenched with water (50 mL). The mixture was extracted with diethyl ether (30 mL), and the organics were washed with saturated aqueous NaCl (50 mL). The organic layer was collected and the residual ether and was removed under vacuum. The remaining benzyl alcohol was removed under vacuum at 100° C. The resulting crude product was then purified by column chromatography eluting with ether in hexanes (50-100%) to yield a clear oil (4.6 g). Note: The starting epoxide contained a mixture of diastereomers (80% SS and 20% SR isomer). The mixture of diastereomers were not separated in this step.

(S)-3-((S)-2-Benzyloxy-1-hydroxyethyl)-pyrrolidine-1-carboxylic acid t-butyl ester (4.6 g, 14 mmol, 10. eq.) was combined with 4-fluorobenzotrifluoride (5.5 mL, 42.9 mmol, 3.0 eq.) in DMF (30 mL, 400 mmol). The mixture was degassed under nitrogen, and NaH (481 mg, 20.0 mmol) was added in small portions. The resulting mixture was stirred for 10 minutes at room temperature, followed by stirring at 90° C. for 3 hours. The mixture was then cooled to room temperature, extracted with hexanes (50 mL), and washed with water (50 mL) then 2M aqueous NaCl (50 mL). The organic layer was collected, stirred in activated carbon (460 mg) for 5 minutes, dried over Na₂SO₄, filtered, and concentrated. The resulting crude oil was dissolved in MeOH (50 mL), and 10% Pd/C (0.1:0.9, Palladium:carbon black, 670 mg, 630 mol) was added under nitrogen. The mixture was stirred under hydrogen (1 atm) overnight. The mixture was filtered and the filtrate was concentrated. The resulting crude oil was dissolved in hexanes (~30 mL) and EtOAc (~15 ml), then concentrated until precipitate formed. Additional hexanes was added and the precipitate was stirred for 15 minutes. The precipitate was filtered and dried to give the title compound as a white solid (3.3 g).

¹H NMR (400 MHz, DMSO): δ (ppm)=7.62 (d, J=8.6 Hz, 2H), 7.17 (d, J=8.6 Hz, 2H), 4.99-4.83 (m, J=5.2 Hz, 1H), 4.52-4.37 (m, 1H), 3.70-3.59 (m, J=12.0, 5.4, 3.8 Hz, 1H), 3.59-3.49 (m, 1H), 3.46-3.33 (m, 2H), 3.24-2.94 (m, 2H), 2.67-2.52 (m, 1H), 2.00-1.86 (m, J=30.7 Hz, 1H), 1.76-1.58 (m, 1H), 1.36 (d, J=13.5 Hz, 8H).

Preparation 4

(S)-3-[(S)-2-Methylamino-1-(4-trifluoromethylphenox)ethyl]pyrrolidine-1-carboxylic Acid t-Butvyl Ester

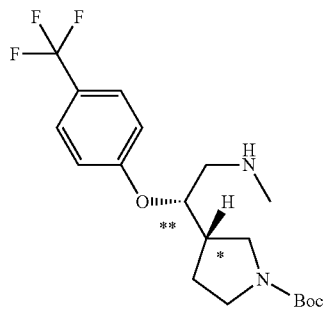 [SMILES: CNC[C@@H](Oc1ccc(C(F)(F)F)cc1)[C@H]1CCN(C(=O)OC(C)(C)C)C1]

(S)-3-[(S)-2-Hydroxy-1-(4-trifluoromethylphenoxy)ethyl]pyrrolidine-1-carboxylic acid t-butyl ester (500 mg, 1.3 mmol, 1.0 eq.) was dissolved in DCM (8.5 mL), and the solution was cooled to 0° C. Triethylenediamine (299 mg, 2.7 mmol) was added, followed by p-toluenesulfonyl chloride (508 mg, 2.7 mmol, 2.0 eq.), and the mixture was stirred at 0° C. for 1 hour. The mixture was diluted with DCM (50 mL) and washed with water (50 mL). The organic layer was dried over $MgSO_4$, filtered, and concentrated to yield a clear oil.

A solution of N-methyltrifluoroacetamide (508 mg, 4.0 mmol) in DMF (2.68 mL) was cooled to 0° C., and LiH (31.8 mg, 4.0 mmol) was added slowly in portions, and the resulting mixture was stirred for 15 minutes. A solution of the clear oil (prepared above) in DMF (5 ml) was then added and the solution was stirred at 60° C. overnight. The mixture was then cooled to room temperature and 1N NaOH (5 mL) was added, followed by DCM (5 mL). The resulting biphasic mixture was shaken vigorously. The layers were separated and the aqueous layer was extracted with DCM (3×10 mL). The combined organic layers were concentrated, then redissolved in 4:1 $H_2O$:AcOH and purified by preparative HPLC to yield the title compound as a TFA salt (160 mg).

$^1$H NMR (400 MHz, $CDCl_3$): δ (ppm)=9.45 (br. s, 1H), 9.20 (br. s, 1H), 7.45 (d, J=12.0 Hz, 2H), 6.93 (d, J=8.0 Hz, 2H), 4.90-4.65 (m, 1H), 4.65-3.80 (m, 2H), 3.45-3.23 (m, 2H), 3.23-2.90 (m, 3H), 2.55-2.37 (m, 1H), 2.37-2.20 (m, 2H), 1.94-1.71 (m, 1H), 1.71-1.49 (m, 1H), 1.33 (s, 9H).

Example 1

Methyl-[(S)-2-(S)-pyrrolidin-3-yl-2-(4-trifluoromethylphenoxy)ethyl]methylsulfonylurea

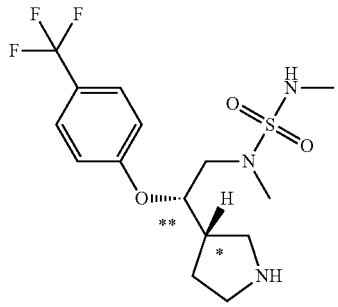 [SMILES: CNS(=O)(=O)N(C)C[C@@H](Oc1ccc(C(F)(F)F)cc1)[C@H]1CCNC1]

(S)-3-[(S)-2-Methylamino-1-(4-trifluoromethylphenoxy)ethyl]pyrrolidine-1-carboxylic acid t-butyl ester (35.0 mg, 90 μmol, 1.0 eq.) was dissolved in DCM (1.2 mL) and triethylamine (64.2 μL), and methylsulfamoyl chloride (26.7 mg, 206 mol, 2.3 eq.) was added. The resulting mixture was stirred for 1 hour at room temperature then concentrated under reduced pressure. The crude material was redissolved in 1.2 M of HCl in EtOH (1.9 mL) and stirred at room temperature overnight. The mixture was again concentrated under reduced pressure then redissolved in 1:1 AcOH/$H_2O$ (1.5 mL) and purified by preparative HPLC to yield the title compound as a TFA salt (0.3 mg). MS m/z: $[M+H]^+$ calcd for $C_{15}H_{22}F_3N_3O_3S$, 382.13. found 382.0.

Preparation 5

(S)-3-[(S)-2-Amino-1-(4-trifluoromethylphenoxy)ethyl]pyrrolidine-1-carboxylic Acid t-Butyl Ester

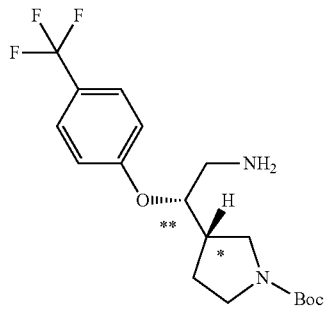 [SMILES: CC(C)(C)OC(=O)N1CC[C@H]([C@@H](CN)Oc2ccc(C(F)(F)F)cc2)C1]

A solution of (S)—(S)-3-oxiranylpyrrolidine-1-carboxylic acid t-butyl ester (1.1 g, 4.9 mmol, 1.0 eq.), sodium azide (800 mg, 12.3 mmol, 2.5 eq.), and ammonium chloride (474 mg, 8.9 mmol) in MeOH (25 mL) was stirred at reflux overnight. The white solid residue obtained on removal of solvent was dissolved in EtOAc (25 mL) and washed with water and saturated aqueous NaCl (1×25 mL each). The organic layer was then dried over $Na_2SO_4$ and concentrated to yield (S)-3-((S)-2-azido-1-hydroxyethyl)pyrrolidine-1-carboxylic acid t-butyl ester (1.3 g).

$^1$H NMR (400 MHz, $CDCL_3$): δ (ppm)=3.76-3.36 (m, 4H), 3.35-3.07 (m, 2H), 2.37-2.16 (m, 1H), 2.04 (s, 1H), 1.93-1.80 (m, 1H), 1.71-1.51 (m, 1H), 1.48-1.36 (m, 9H).

(S)-3-((S)-2-Azido-1-hydroxyethyl)pyrrolidine-1-carboxylic acid t-butyl ester (1.3 g, 5.0 mmol, 1.0 eq.) was combined with DMF (18 mL). Washed and dried NaH (362 mg, 15.1 mmol, 3.0 eq.) was carefully added in 3 separate portions. The resulting mixture was stirred at room temperature for 15 minutes under nitrogen. 4-Fluorobenzotrifluoride (1.9 mL, 15.1 mmol, 3.0 eq.) was added and the mixture was stirred at 100° C. for 3 hours. The mixture was then concentrated under reduced pressure. The resulting material was dissolved in EtOAc (15 mL) and washed with water (1×15 mL). The organic layer was concentrated and purified by flash chromatography (0-100% EtOAc/hexanes) to yield (S)-3-[(S)-2-azido-1-(4-trifluoromethylphenoxy)ethyl]-pyrrolidine-1-carboxylic acid t-butyl ester (1.4 g).

$^1$H NMR (400 MHz, $CDCL_3$): δ (ppm)=7.65-7.47 (m, 2H), 7.09-6.95 (m, 2H), 4.40 (dd, J=10.0, 6.3 Hz, 1H), 3.77-3.62 (m, 1H), 3.62-3.49 (m, 2H), 3.49-3.39 (m, 1H), 3.39-3.25 (m, 1H), 3.20 (dd, J=20.0, 9.8 Hz, 1H), 2.77-2.57 (m, 1H), 2.03-1.91 (m, 1H), 1.69 (dd, J=19.7, 10.4 Hz, 1H), 1.50-1.36 (m, 9H).

(S)-3-[(S)-2-Azido-1-(4-trifluoromethylphenoxy)ethyl]pyrrolidine-1-carboxylic acid t-butyl ester (2.10 g, 5.24 mmol) was combined with 10% Pd/C, Degussa type, wet 50% (0.05:0.45:0.5, Palladium:carbon black:$H_2O$, 1.1 g, 520 μmol) and EtOH (240 mL). The mixture was stirred under an atmosphere of hydrogen (1 atm) at room temperature for 1 hour. The catalyst was then removed by filtration through Celite (MeOH wash) and the filtrate was concentrated to yield the title compound (1.8 g).

¹H NMR (400 MHz, CDCL₃): δ (ppm)=7.53 (t, J=6.4 Hz, 2H), 7.02 (d, J=6.5 Hz, 2H), 4.33 (s, 1H), 3.68-3.56 (m, 1H), 3.56-3.35 (m, 2H), 3.36-3.22 (m, 1H), 3.20-3.10 (m, 1H), 3.10-2.99 (m, 1H), 2.99-2.85 (m, 1H), 2.64 (dt, J=17.4, 9.4 Hz, 1H), 2.04-1.85 (m, 1H), 1.80-1.47 (m, 2H), 1.43 (s, 9H).

Example 2

4-Oxazol-5-yl-N—[(S)-2-(S)-pyrrolidin-3-yl-2-(4-trifluoromethylphenoxy)ethyl]benzenesulfonamide

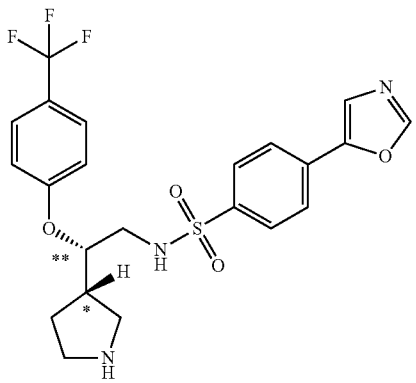 [SMILES: O=S(=O)(NC[C@@H](Oc1ccc(C(F)(F)F)cc1)[C@H]1CCNC1)c1ccc(-c2cnco2)cc1]

(S)-3-[(S)-2-Amino-1-(4-trifluoromethylphenoxy)ethyl]pyrrolidine-1-carboxylic acid t-butyl ester (35.0 mg, 0.093.5 mol, 1.0 eq.) was dissolved in DCM (1.2 mL) and triethylamine (39.1 μL). A solution of 4-(1,3-oxazol-5-yl)benzenesulfonyl chloride (56.9 mg, 234 μmol, 2.5 eq.) in DCM (0.4 mL,) was then added. The resulting mixture was stirred for 1 hour at room temperature. Saturated sodium bicarbonate was then added (1 mL) and the mixture was diluted with DCM (2 mL). The organic layer was collected and concentrated under reduced pressure. The crude material was redissolved in 1.2 M of HCl in EtOH (1.9 mL) and stirred at room temperature overnight. The mixture was then concentrated under reduced pressure then redissolved in 1:1 AcOH/H₂O (1.5 mL) and purified by preparative HPLC to yield the title compound as a TFA salt (20.1 mg). MS m/z: [M+H]⁺ calcd for C₂₂H₂₂F₃N₃O₄S, 482.13. found 482.4.

Example 3

Following the procedures described in the examples above, and substituting the appropriate starting materials and reagents, compounds 3-1 to 3-35, having formula IIIb, were prepared as HCl or TFA salts:

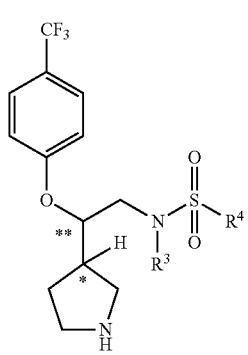

(IIIb)

| Ex. | R³ | R⁴ | Formula | MS m/z: [M + H]⁺ calcd | found |
|---|---|---|---|---|---|
| 1 | H | —CH₃ | C₁₄H₁₉F₃N₂O₃S | 353.11 | 353.0 |
| 2 | H | —CH₃ | C₁₄H₁₉F₃N₂O₃S | 353.11 | 353.0 |
| 3 | —CH₃ | —CH₃ | C₁₅H₂₁F₃N₂O₃S | 367.12 | 367.4 |
| 4 | —C(O)CH₃ | —CH₃ | C₁₆H₂₁F₃N₂O₄S | 395.12 | 395.0 |
| 5 | H | —CH₂CH₃ | C₁₅H₂₁F₃N₂O₃S | 367.12 | 367.0 |
| 6 | —CH₃ | —CH₂CH₃ | C₁₆H₂₃F₃N₂O₃S | 381.14 | 381.0 |
| 7 | H | —CH(CH₃)₂ | C₁₆H₂₃F₃N₂O₃S | 381.14 | 381.0 |
| 8 | H | cyclopropyl | C₁₆H₂₁F₃N₂O₃S | 379.12 | 379.0 |
| 9 | H | —NH₂ | C₁₃H₁₈F₃N₃O₃S | 354.10 | 354.0 |
| 10 | H | —NH₂ | C₁₃H₁₈F₃N₃O₃S | 354.10 | 354.0 |
| 11 | H | —N(CH₃)₂ | C₁₅H₂₂F₃N₃O₃S | 382.13 | 382.5 |
| 12 | H | —CH₂SO₂—CH₃ | C₁₅H₂₁F₃N₂O₅S₂ | 431.08 | 431.5 |
| 13 | H | 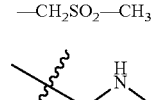 | C₁₆H₁₉F₃N₄O₃S | 405.11 | 405.0 |
| 14 | H |  | C₁₇H₂₁F₃N₄O₃S | 419.13 | 419.4 |

-continued
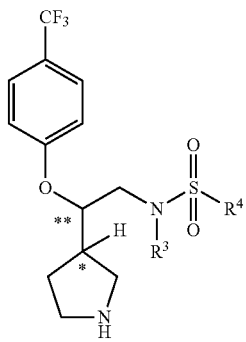
(IIIb)
| | | | | MS m/z: [M + H]⁺ | |
|---|---|---|---|---|---|
| Ex. | R³ | R⁴ | Formula | calcd | found |
| 15 | H | 1H-1,2,4-triazol-3-yl | $C_{15}H_{18}F_3N_5O_3S$ | 406.11 | 406.0 |
| 16 | H | benzo[c][1,2,5]oxadiazol-4-yl | $C_{19}H_{19}F_3N_4O_4S$ | 457.11 | 457.0 |
| 17 | H | morpholino | $C_{17}H_{24}F_3N_3O_4S$ | 424.14 | 424.0 |
| 18 | H | phenyl | $C_{19}H_{21}F_3N_2O_3S$ | 415.12 | 415.6 |
| 19 | H | phenyl | $C_{19}H_{21}F_3N_2O_3S$ | 415.12 | 415.7 |
| 20 | H | 4-cyanophenyl | $C_{20}H_{20}F_3N_3O_3S$ | 440.12 | 440.0 |
| 21 | H | 4-carboxyphenyl | $C_{20}H_{21}F_3N_2O_5S$ | 459.11 | 459.0 |
| 22 | H | 4-nitrophenyl | $C_{19}H_{20}F_3N_3O_5S$ | 460.11 | 460.0 |

-continued
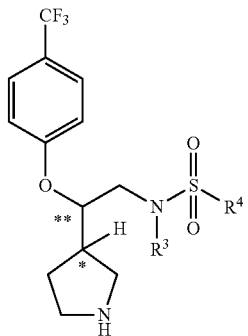
(IIIb)
| Ex. | R³ | R⁴ | Formula | MS m/z: [M + H]⁺ calcd | found |
|---|---|---|---|---|---|
| 23 | H | ⸺C₆H₄-OCH₃ (4-OMe phenyl) | $C_{20}H_{23}F_3N_2O_4S$ | 445.13 | 445.5 |
| 24 | H | ⸺C₆H₄-(CH₂)₂OCH₃ (4-substituted phenyl) | $C_{22}H_{27}F_3N_2O_4S$ | 473.16 | 473.0 |
| 25 | H | 3-(C(O)NHCH₃)phenyl | $C_{21}H_{24}F_3N_3O_4S$ | 472.14 | 472.0 |
| 26 | H | 3-(NHC(O)CH₃)phenyl | $C_{21}H_{24}F_3N_3O_4S$ | 472.14 | 472.0 |
| 27 | H | 4-(SO₂CH₃)phenyl | $C_{20}H_{23}F_3N_2O_5S_2$ | 493.10 | 493.2 |
| 28 | H | 3-(SO₂CH₃)phenyl | $C_{20}H_{23}F_3N_2O_5S_2$ | 493.10 | 493.0 |
| 29 | H | 2-(SO₂CH₃)phenyl | $C_{20}H_{23}F_3N_2O_5S_2$ | 493.10 | 493.0 |
| 30 | H | 4-(SO₂NH₂)phenyl | $C_{19}H_{22}F_3N_3O_5S_2$ | 494.10 | 494.0 |
| 31 | H | 4-(SO₂NHCH₃)phenyl | $C_{20}H_{24}F_3N_3O_5S_2$ | 508.11 | 508.2 |

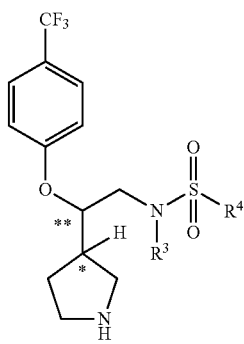

(IIIb)

| Ex. | R³ | R⁴ | Formula | MS m/z: [M + H]⁺ calcd | found |
|---|---|---|---|---|---|
| 32 | H | ⸺⟨phenyl⟩-N-pyrazole | $C_{22}H_{23}F_3N_4O_3S$ | 481.14 | 481.2 |
| 33 | H | ⸺⟨phenyl⟩-N-(3,5-dimethylpyrazole) | $C_{24}H_{27}F_3N_4O_3S$ | 509.18 | 509.2 |
| 34 | H | ⸺⟨phenyl⟩-pyrimidin-2-yl | $C_{23}H_{23}F_3N_4O_3S$ | 493.14 | 493.2 |
| 35 | H | ⸺⟨phenyl⟩-tetrazol-5-yl | $C_{20}H_{21}F_3N_6O_3S$ | 483.14 | 483.5 |

1. N-[(S)-2-(S)-Pyrrolidin-3-yl-2-(4-trifluoromethylphenoxy)ethyl]-methanesulfonamide
2. N-[(R)-2-(S)-Pyrrolidin-3-yl-2-(4-trifluoromethylphenoxy)ethyl]-methanesulfonamide
3. N-Methyl-N-[(S)-2-(S)-pyrrolidin-3-yl-2-(4-trifluoromethylphenoxy)ethyl]-methanesulfonamide
4. N-Acetyl-N-[(S)-2-(S)-pyrrolidin-3-yl-2-(4-trifluoromethylphenoxy)ethyl]-methanesulfonamide
5. Ethanesulfonic acid [(S)-2-(S)-pyrrolidin-3-yl-2-(4-trifluoromethylphenoxy)-ethyl]amide
6. Ethanesulfonic acid melhyl-[(S)-2-(S)-pyrrolidin-3-yl-2-(4-trifluoromethylphenoxy)ethyl]amide
7. Propane-2-sulfonic acid [(S)-2-(S)-pyrrolidin-3-yl-2-(4-trifluoromethylphenoxy)ethyl]amide
8. Cyclopropanesulfonic acid [(S)-2-(S)-pyrrolidin-3-yl-2-(4-trifluoromethylphenoxy)ethyl]amide
9. N-[(S)-2-(S)-Pyrrolidin-3-yl-2-(4-trifluoromethylphenoxy)ethyl]sulfonylurea
10. N[(S)-2-(S)-pyrrolidin-3-yl-2-(4-trifluoromethylphenoxy)ethyl]sulfonylurea
11. N-[(S)(-2-(S)-pyrrolidin-3-yl-2-(4-trifluoromethylphenosxy)ethyl]-N,N-dimethylsulfonylures
12. C-Methanesulfonyl-N-[(S)-2-(S)-pyrrolidin-3-yl-2-(4-trifluoromethylphenoxy)ethyl]methanesulfonamide
13. 3H-Imidazole-4-sulfonic acid [(S)-2-(S)-pyrrolidin-3-yl-2-(4-trifluoromethylphenoxy)ethyl]amide
14. 3-Methyl-3H-imidazole-4-sulfonic acid [(S)-2-(S)-pyrrolidin-3-yl-2-(4-trifluoromethylphenoxy)ethyl]amide
15. 2H-[1,2,4]Triazole-3-sulfonic acid [(S(-2-(S)-pyrrolidin-3-yl-2-(4-trifluoromethylphenoxy)ethyl)amide
16. Benzo[1,2,5]oxadiazole-4-sulfonic acid [(S)-2-(S)-pyrrolidin-3-yl-2-(4-trifluoromethylphenoxy)ethyl]amide
17. Morpholine-4-sulfonic acid [(S)-2-(S)-pyrrolidin-3-yl-2-(4-trifluoromethylphenoxy)ethyl]amide
18. N-[(R)-2-(S)-Pyrrolidin-3-yl-2-(4-trifluoromethylphenoxy)ethyl]benzenesulfonamide
19. N-[(S)-2-(S)-Pyrrolidin-3-yl-2-(4-trifluoromethylphenoxy)ethyl]benzenesulfonamide
20. 4-Cyano-N-[(S)-2-(S)-pyrrolidin-3-yl-2-(4-trifluoromethylphenoxy)ethyl]benzenesulfonamide
21. 4-[(S)-2-(S)-Pyrrolidin-3-yl-2-(4-trifluoromethylphenoxy)ethylsulfamoyl]-benzoic acid
22. 4-Nitro-N-[(S)-2-(S)-pyrrolidin-3-yl-2-(4-trifluoromethylphenoxy)ethyl]benzenesulfonamide
23. 4-Methoxy-N-[(S)-2-(S)-pyrrolidin-3-yl-2-(4-trifluoromethylphenoxy)ethyl]benzenesulfonamide
24. 4-(2-Methoxyethyl)-N-[(S)-2-(S)-pyrrolidin-3-yl-2-(4-trifluoromethylphenoxy)ethyl]benzenesulfonamide
25. N-Methyl-3-[(S)-2-(S)--pyrrolidin-3-yl-2-(4-trifluoromethylphenoxy)ethylsulfamoyl]benamide
26. N-{3-[(S)-2-(S)-Pyrrolidin-3-yl-2-(4-trifluoromethylphenoxy)ethylsulfamoyl]phenyl}acetamide 27. 4-Methanesulfonyl-N-[(S)-2-(S)-pyrrolidin-3-yl-2-(4-trifluoromethylphenoxy)ethyl]benzenesulfonamide
28. 3-Methanesulfonyl-N-[(S)-2-(S)-pyrrolidin-3-yl-2-(4-trifluoromethylphenoxy)ethyl]benzenesulfonamide
29. 2-Methanesulfonyl-N-[(S)-2-(S)-pyrrolidin-3-yl-2-(4-trifluoromethylphenoxy)ethyl]benzenesulfonamide
30. Benzene-1,4-disulfonic acid 1amide 4-{[(S)-2-(S)-pyrrolidin-3-yl-2-(4-trifluoromethylphenoxy)ethyl]amide}
31. Benzene-1,4-disulfonic acid 1-methylamide 4-{[(S)-2-(S)-pyrrolidin-3-yl-2-(4-trifluoromethylphenoxy)ethyl]amide}
32. 4-Pyrazol-1-yl-N-[(S)-2-(S)-pyrrolidin-3-yl-2-(4-trifluoromethylphenoxy)ethyl]benzenesulfonamide
33. 4-(3,5-Dimethyl-pyrazol-1-yl)-N-(S)-2-(S)-pyrrolidin-3-yl-2-(4-trifluoromethylphenoxy)ethyl]benzenesulfonamide
34. 4-Pyrimidin-2-yl-N-[(S)-2-(S)-pyrrolidin-3-yl-2-(4-trifluoromethylphenoxy)ethyl]benzenesulfonamide
35. N[(S)-2-(S)-Pyrrolidin-3-yl-2-(4-trifluoromethylphenoxy)ethyl]-4-(1H-tetrazol-5-yl)-benzenesulfonamide Preparation 6

(S)-3-[(S)-2-Chlorosulfonyl-1-(4-trifluoromethylphenoxy)ethyl]pyrrolidine-1-carboxylic acid t-Butyl Ester

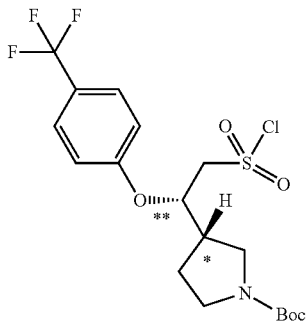 [SMILES: CC(C)(C)OC(=O)N1CC[C@H]([C@@H](CS(=O)(=O)Cl)Oc2ccc(C(F)(F)F)cc2)C1]

(S)-3-[(S)-2-Hydroxy-1-(4-trifluoromethylphenoxy)ethyl]pyrrolidine-1-carboxylic acid t-butyl ester (200 mg, 0.5 mmol, 1.0 eq.) was dissolved in triethylenediamine (65.7 mg, 586 mol) in DCM (3 mL), and the solution was cooled to 0° C. Tosic anhydride (182 mg, 559 µmol, 1.0 eq.) was added, and the mixture was stirred at room temperature for 1 hour. The mixture was washed with water (2×3 mL). The organic layer was collected, dried over Na$_2$SO$_4$, filtered, and concentrated.

The crude product was dissolved in EtOH (4 mL). Potassium thioacetate (63.9 mg, 559 µmol) was added and the resulting mixture was stirred at 50° C. for 3 days. The mixture was then concentrated and extracted with hexanes (5 mL) and water (5 mL). The black residue that formed during extraction was filtered. The organic layer was separated and washed with water (5 mL), then collected, dried over Na$_2$SO$_4$, filtered, and concentrated.

The crude product was dissolved in MeCN (0.5 mL) and added dropwise to a solution of N-chlorosuccinimide (284 mg, 2.1 mmol) in MeCN (1.5 mL) and 2 M of HCl in water (750 µL) at 0° C. The mixture was stirred for 1 hour then extracted with diisopropyl ether (10 mL) and water (10 mL). The aqueous layer was washed with diisopropyl ether (10 mL). The organic layers were combined and concentrated until dry to yield the title compound (220 mg), which was used without further purification.

Example 4

(S)-2-(S)-Pyrrolidin-3-yl-2-(4-trifluoromethylphenoxy)ethanesulfonic Acid Amide

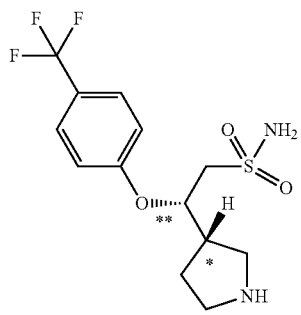 [SMILES: NS(=O)(=O)C[C@@H](Oc1ccc(C(F)(F)F)cc1)[C@H]1CCNC1]

(S)-3-[(S)-2-Chlorosulfonyl-1-(4-trifluoromethylphenoxy)ethyl]pyrrolidine-1-carboxylic acid t-butyl ester (50 mg, 109 µmol, 1.0 eq.) in DCM (1.0 mL) was combined with 0.5 M of ammonia in 1,4-dioxane (874 µL, 4.0 eq.) and the resulting mixture was stirred at room temperature for 2 hours. TFA (1.0 mL) was added and stirred for 1 minute. The mixture was then concentrated and purified by preparative HPLC to yield the title compound as a TFA salt (16.3 mg). MS m/z: [M+H1]$^+$ calcd for $C_{13}H_{17}F_3N_2O_3S$, 339.09; found 339.0.

Example 5

(S)-2-(S)-Pyrrolidin-3-yl-2-(4-trifluoromethylphenoxy)ethanesulfonic Acid Benzylamide

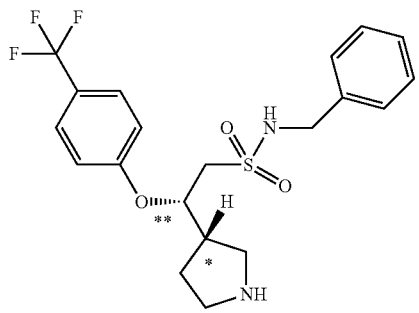 [SMILES: O=S(=O)(C[C@@H](Oc1ccc(C(F)(F)F)cc1)[C@H]1CCNC1)NCc1ccccc1]

(S)-3-[(S)-2-Chlorosulfonyl-1-(4-trifluoromethylphenoxy)ethyl]pyrrolidine-1-carboxylic acid t-butyl ester (50 mg, 109 µmol, 1.0 eq.) in DCM (1.0 mL) was combined with benzylamine (47.7 µL, 4.0 eq.) and the resulting mixture was stirred at room temperature for 2 hours. TFA (1.0 mL) was added and stirred for 1 minute. The mixture was then concentrated and purified by preparative HPLC to yield the title compound as a TFA salt (7.3 mg). MS m/z: [M+H]$^+$ calcd for $C_{20}H_{23}F_3N_2O_3S$, 429.14. found 429.0.

Example 6

(S)-2-(S)-Pyrrolidin-3-yl-2-(4-trifluoromethylphenoxy)ethanesulfonic Acid Methylamide

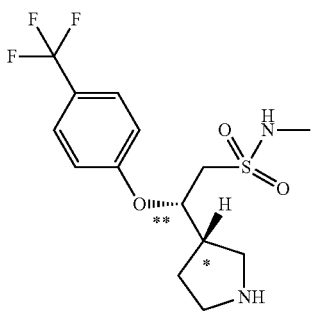 [SMILES: CNS(=O)(=O)C[C@@H](Oc1ccc(C(F)(F)F)cc1)[C@H]1CCNC1]

(S)-3-[(S)-2-Chlorosulfonyl-1-(4-trifluoromethylphenoxy)ethyl]pyrrolidine-1-carboxylic acid t-butyl ester (50 mg, 109 µmol, 1.0 eq.) in DCM (1.0 mL) was combined with a solution of methylamine (2M in THF; 4.0 eq) and the resulting mixture was stirred at room temperature for 2 hours. TFA (1.0 mL) was added and stirred for 1 minute. The mixture was then concentrated and purified by preparative HPLC to yield the title compound as a TFA salt (8.7 mg). MS m/z: $[M+H]^+$ calcd for $C_{14}H_{19}F_3N_2O_3S$, 353.11. found 353.0.

Example 7

Following the procedures described in the examples above, and substituting the appropriate starting materials and reagents, compound 7-1, having formula IVb, was prepared as a TFA salt:

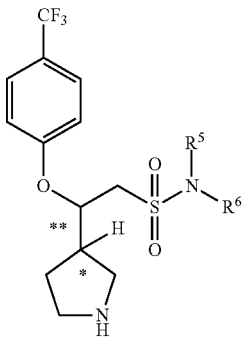

(IVb)

| Ex. | $R^5$ | $R^6$ | Formula | MS m/z: $[M+H]^+$ calcd | found |
|---|---|---|---|---|---|
| 1 | —CH$_3$ | —CH$_3$ | $C_{15}H_{21}F_3N_2O_3S$ | 367.12 | 367.0 |

1. (S)-2-(S)-Pyrrolidin-3-yl-2-(4-trifluoromethylphenoxy) ethanesulfonic acid dimethylamide

Assay 1 hSERT Binding Assay

Membrane radioligand binding assays were used to measure inhibition of labeled ligand ($^3$H-citalopram) binding to membranes prepared from cells expressing the human recombinant serotonin transporter (hSERT) in order to determine the $pK_i$ values of test compounds at the transporters.

Membrane Preparation from Cells Expressing hSERT

Recombinant human embryonic kidney (HEK-293) derived cell lines stably transfected with hSERT, were grown in Dulbecco's Modified Eagle's Medium supplemented with 10% dialyzed fetal bovine serum, 100 µg/ml penicillin, 100 µg/ml streptomycin, 2 mM L-glutamine and 250 g/ml of the aminoglycoside antibiotic G418, in a 5% $CO_2$ humidified incubator at 37° C. When cultures reached 80% confluence, the cells were washed thoroughly in phosphate buffered saline (without $Ca^{2+}$ and $Mg^{2+}$) and lifted with 5 mM ethylenediaminetetraacetic acid in phosphate buffered saline. Cells were pelleted by centrifugation, resuspended in lysis buffer (10 mM Tris-HCl, pH7.5 containing 1 mM ethylenediaminetetraacetic acid), homogenized, pelleted by centrifugation, and then resuspended in 50 mM Tris-HCl, pH 7.5 and 10% sucrose at 4° C. Protein concentration of the membrane suspension was determined using a Bio-Rad Bradford Protein Assay kit. Membranes were snap frozen and stored at –80° C.

Binding Assay

Binding assays were performed in a 96-well assay plate in a total volume of 200 µl assay buffer (50 mM Tris-HCl, 120 mM NaCl, 5 mM KCl, pH 7.4) with 0.5-1 µg membrane protein. Saturation binding studies, to determine radioligand $K_d$ values for $^3$H-citalopram were conducted using 12 different radioligand concentrations ranging from 0.005-10 nM. Inhibition assays for determination of $pK_i$ values of test compounds were conducted with $^3$H-citalopram at 11 different concentrations of test compound ranging from 10 µM to 100 µM.

Stock solutions (10 mM in DMSO) of test compound were prepared and serial dilutions made using Dilution Buffer (50 mM Tris-HCl, 120 mM NaCl, 5 mM KCl, pH 7.4, 0.1% bovine serum albumin, 400 µM ascorbic acid). Non-specific radioligand binding was determined in the presence of 1 µM duloxetine (in Dilution Buffer).

Following a 60 minute incubation at 22° C. (or a period sufficient to reach equilibrium), the membranes were harvested by rapid filtration over a 96-well UniFilter GF/B plate, pretreated with 0.3% polyethyleneimine, and washed 6 times with 300 µl wash buffer (50 mM Tris-HCl, 0.9% NaCl). Plates were dried overnight at room temperature, –45 µl of MicroScint™-20 (Perkin Elmer) added and bound radioactivity quantitated via liquid scintillation spectroscopy. Inhibition curves and saturation isotherms were analyzed using GraphPad Prism Software package (GraphPad Software, Inc., San Diego, Calif.). $IC_{50}$ values were generated from concentration response curves using the Sigmoidal Dose Response (variable slope) algorithm in Prism GraphPad. $K_d$ and $B_{max}$ values for the radioligand were generated from saturation isotherms using the Saturation Binding Global Fit algorithm in Prism GraphPad. $pK_i$ (negative decadic logarithm of $K_i$) values for test compounds were calculated from the best-fit $IC_{50}$ values, and the $K_d$ value of the radioligand, using the Cheng-Prusoff equation (Cheng & Prusoff (1973) *Biochem. Pharmacol.* 22(23):3099-3108): $K_i=IC_{50}/(1+[L]/K_d)$, where [L]=concentration radioligand.

Exemplary compounds of the invention were tested in this assay and were found to exhibit SERT $pK_i$ values as indicated below.

| Ex. | SERT p$K_i$ |
|---|---|
| 3-1 | ≥8.0 |
| 3-4 | ≥8.0 |
| 3-9 | ≥8.0 |
| 3-21 | ≥7.0 |

Assay 2 hSERT Neurotransmitter Uptake Assay

Neurotransmitter uptake assays were used to measure inhibition of $^3$H-serotonin ($^3$H-5-hydroxytryptamine) uptake into cells expressing hSERT in order to determine the p$IC_{50}$ values of test compounds at the transporter, similar to the procedures described in Tsuruda et al. (2010) *Journal of Pharmacological and Toxicological Methods* 61(2): 192-204.

HEK293 cells stably-transfected with human recombinant SERT (HEK293-hSERT) were grown in Dulbecco's Modified Eagle's Medium supplemented with 10% dialyzed fetal bovine serum, 100 g/ml penicillin, 100 g/ml streptomycin, 2 mM L-glutamine, and 250 μg/ml of the aminoglycoside antibiotic G418. Cells were incubated in a 5% $CO_2$, humidified incubator at 37° C.

The neurotransmitter uptake assay was performed in a 96-well assay plate in a total volume of 100 μL assay buffer containing HEK293-hSERT cells (7500-10,000 cells/well; plated ~2 hours prior to assay initiation. Neurotransmitter Transporter Uptake Assay dye (0.5 μM), and eleven different concentrations of compound ranging from 10 pM to 100 μM was used. Non-specific uptake was determined in the presence of indatraline (2.5 μM). The final assay buffer was 12.5 mM Tris-HCl, 5 mM 4-(2-hydroxyethyl)-1-piperazineethanesulfonic acid, 3 mM $NaHCO_3$, 0.3 mM $KH_2PO_4$, 0.25 mM $Na_2HPO_4$, 130 mM NaCl, 5 mM KCl, 1 mM $CaCl_2$, 0.4 mM $MgCl_2$, 0.3 mM $MgSO_4$, 4 mM D-glucose, 0.025% bovine serum albumin, 0.1 mM ascorbic acid, pH 7.4.

In pre-incubation studies, test compound was added to cells for 30 minutes at 37° C. prior to the addition of fluorescent substrate. For determination of inhibitory potency, a 10-30 minute endpoint substrate accumulation was determined by fluorescence spectroscopy using a Safire (Tecan Group Ltd., Minnendorf, Switzerland) and analysis was performed as described in Tsuruda et al., supra. For real-time measurements, compounds were either preincubated (as above) or mixed with substrate prior to addition, and kinetic measurements, relative fluorescence units (RFU integrated over 0.5 ms),were made using a cycle time of 1 min.

Compounds of the invention that were tested in this assay were found to have serotonin reuptake inhibition p$IC_{50}$ values as follows:

| Ex. | SERT p$IC_{50}$ |
|---|---|
| 1 | ≥8.0 |
| 2 | ≥8.0 |
| 3-1 | ≥8.0 |
| 3-2 | ≥7.0 |
| 3-3 | ≥8.0 |
| 3-4 | ≥8.0 |
| 3-5 | ≥8.0 |
| 3-6 | ≥8.0 |
| 3-7 | ≥7.0 |
| 3-8 | ≥8.0 |
| 3-9 | ≥8.0 |
| 3-10 | ≥7.0 |
| 3-11 | ≥8.0 |
| 3-12 | ≥8.0 |
| 3-13 | ≥7.0 |
| 3-14 | ≥7.0 |
| 3-15 | ≥7.0 |
| 3-16 | ≥8.0 |
| 3-17 | ≥8.0 |
| 3-18 | ≥8.0 |
| 3-19 | ≥8.0 |
| 3-20 | ≥8.0 |
| 3-21 | ≥7.0 |
| 3-22 | ≥8.0 |
| 3-23 | ≥8.0 |
| 3-24 | ≥8.0 |
| 3-25 | ≥8.0 |
| 3-26 | ≥8.0 |
| 3-27 | ≥8.0 |
| 3-28 | ≥7.0 |
| 3-29 | ≥8.0 |
| 3-30 | ≥8.0 |
| 3-31 | ≥8.0 |
| 3-32 | ≥8.0 |
| 3-33 | ≥8.0 |
| 3-34 | ≥8.0 |
| 3-35 | ≥7.0 |
| 4 | ≥8.0 |
| 5 | ≥8.0 |
| 6 | ≥8.0 |
| 7-1 | ≥8.0 |

Assay 3

Ex Vivo SERT Radioligand Binding Assay

Ex vivo radioligand binding assays are used to determine the in vivo occupancy of SERT, in selected brain regions, following in vivo administration (acute or chronic) of test compounds. Following administration of test compound (by intravenous, intraperitoneal, oral, subcutaneous or other route) at the appropriate dose (0.0001 to 100 mg/kg), rats (≥n=4 per group) are euthanized at specific time points (10 minutes to 48 hours) by decapitation and the brain dissected on ice. Relevant brain regions are dissected, frozen, and stored at −80° C. until use.

For the ex vivo radioligand binding assay, the initial rate of association of the SERT selective radioligand ($^3$H-citalopram) with rat brain crude homogenates, prepared from vehicle and test compound-treated animals, is monitored (see Hess et al. (2004) *J. Pharmacol. Exp. Ther.* 310(2):488-497). Crude brain tissue homogenates are prepared by homogenizing frozen tissue pieces in 0.15 ml (per mg wet weight) of 50 mM Tris-HCl, 120 mM NaCl, 5 mM KCl, pH 7.4 buffer. Radioligand association assays are performed in a 96-well assay plate in a total volume of 200 μl assay buffer (50 mM Tris-HCl, 120 mM NaCl, 5 mM KCl, 0.025% bovine serum albumin, pH 7.4) with 650 g wet weight tissue (equivalent to 25 μg protein). Homogenates are incubated for up to 5 minutes with $^3$H-citalopram (3 nM) prior to termination of the assay by rapid filtration over a 96-well UniFilter GF/B plate, pretreated with 0.3% polyethyleneimine. Filters are then washed 6 times with 300 μl wash buffer (50 mM Tris-HCl, 0.9% NaCl, pH 7.4 at 4° C.). Non-specific radioligand binding is determined in the presence of 1 μM duloxetine. The plates are dried overnight at room temperature, −45 μl of MicroScint™-20 (Perkin Elmer) added and bound radioactivity quantitated via liquid scintillation spectroscopy. The initial rate of association of $^3$H-citalopram is determined by linear regression using GraphPad Prism Software package (GraphPad Software, Inc., San Diego, Calif.). The average rate of radioligand association to brain tissue homogenates from vehicle-treated animals is determined. The % occupancy of test compounds is then determined using the following equation:

% occupancy=100×(1−(initial rate association for test compound-treated tissue/mean rate association for vehicle-treated tissue))

$ED_{50}$ values are determined by plotting the log 10 of the dose of the test compound against the % occupancy. $ED_{50}$ values are generated from concentration response curves using the Sigmoidal Dose Response (variable slope) algorithm in GraphPad Prism.

Assay 4

Peripheral Selectivity

Fed male Sprague-Dawley rats (n=1/timepoint) are dosed orally with a test compound. Blood (via cardiocentesis), cerebrospinal fluid (CSF) (via cisternae magna) and brain are collected from an animal at 0.5, 1, 2, 4, 8 and 24 hours post-dose. Total plasma, CSF and brain concentrations are determined by LC-MS/MS. The pharmacokinetic parameters are assessed by non-compartmental methods using WinNonlin (Version 5.3, Pharsight, Mountain View, Calif.). The unbound fraction in plasma and brain is determined by equilibrium dialysis. Free plasma and free brain concentrations are determined by multiplying the total concentration in plasma or brain by its respective unbound fraction. CSF is assumed to be unbound, due to the absence of protein. Peripheral selectivity is assessed by comparing the unbound exposures ($C_{max}$ and AUC) in free plasma versus CSF and/or free brain. Test compounds are considered to be peripherally selective if they exhibit a ratio of free plasma concentration: free brain concentration (measured by the AUC) greater than 10.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety to the same extent as if each document had been individually incorporated by reference herein.

What is claimed is:

1. A method of treating a disease selected from pulmonary arterial hypertension, gastrointestinal disorders, cancer, rheumatoid arthritis, osteoarthritis, osteoporosis, and diabetes, comprising administering a therapeutically effective amount of a compound of formula I:

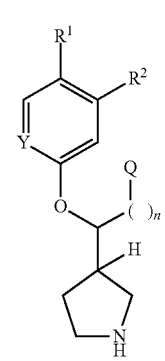

where:
Y is —CH— or —N—;
$R^1$ is selected from halo; —$C_{1-6}$alkyl optionally substituted with 1 to 5 fluoro atoms; —O—$C_{1-6}$alkyl optionally substituted with 1 to 5 fluoro atoms; —$C_{1-6}$alkylene-phenyl; —O—$C_{0-3}$alkylene-phenyl; —SO—$C_{1-6}$alkyl; —C(O)NH$_2$; and —NO$_2$;
$R^2$ is selected from hydrogen, halo, and —CN;
n is an integer from 1 to 3;
Q is selected from —NR$^3$SO$_2$R$^4$ and —SO$_2$NR$^5$R$^6$;
$R^3$ is selected from hydrogen, —$C_{1-6}$alkyl, and —C(O)$C_{1-6}$alkyl;
$R^4$ is selected from —$C_{1-6}$alkyl; —$C_{3-6}$cycloalkyl; —NR$^7$R$^5$; —CH$_2$SO$_2$—$C_{1-6}$alkyl pyrazole optionally substituted with —CH$_3$; triazole; morpholine; benzoxadiazole; and phenyl optionally substituted with $R^9$; where $R^7$ and $R^8$ are independently selected from hydrogen and —$C_{1-6}$alkyl; and $R^9$ is selected from —CN, —COOH, —NO, —$C_{0-2}$alkylene-O—$C_{1-6}$alkyl, —C(O)NR$^7$R$^8$, —NR$^7$C(O)—$C_{1-6}$alkyl, —SO$_2$—$C_{1-6}$alkyl, —SO$_2$—NR$^7$R$^8$, and a nitrogen-containing heteroaryl optionally substituted with 1 or 2-CH$_3$ groups;
$R^5$ is selected from hydrogen and —$C_{1-6}$alkyl; and
$R^6$ is selected from hydrogen, —$C_{1-6}$alkyl, and benzyl;
or a pharmaceutically acceptable salt thereof.

2. The method of claim 1, where Y is —CH—.
3. The method of claim 1, where $R^1$ is selected from —$C_{1-6}$alkyl optionally substituted with 1 to 5 fluoro atoms, —O—$C_{1-6}$alkyl optionally substituted with 1 to 5 fluoro atoms, and —NO$_2$.
4. The method of claim 3, where $R^1$ is —$C_{1-6}$alkyl optionally substituted with 1 to 5 fluoro atoms.
5. The method of claim 4, where $R^1$ is —CF$_3$.
6. The claim 1, where $R^2$ is selected from hydrogen and —CN.
7. The method of claim 1, where $R^2$ is hydrogen.
8. The method of claim 1, where n is 1.
9. The method of claim 1, where Q is —NR$^3$SO$_2$R$^4$.
10. The method of claim 9, where $R^3$ is selected from hydrogen, —CH$_3$, and —C(O)CH$_3$.
11. The method of claim 9, where $R^4$ is selected from —CH$_3$; —CH$_2$CH$_3$; —CH(CH$_3$)$_2$; cyclopropyl; —NH$_2$; —NH(CH$_3$); —N(CH$_3$)$_2$; —CH$_2$SO$_2$—CH$_3$; pyrazole; pyrazole substituted with —CH$_3$; triazole; morpholine; benzoxadiazole; and phenyl optionally substituted with $R^9$; where $R^9$ is selected from —CN, —COOH, —NO$_2$, —OCH$_3$, —C(O)NHCH$_3$, —NHC(O)CH$_3$, —SO$_2$—CH$_3$, —SO$_2$—NH$_2$, —SO$_2$—NHCH$_3$, oxazole, pyrimidine, tetrazole, pyrazole, and pyrazole substituted with two methyl groups.

12. The method of claim 1, where Q is —SO$_2$NRSR$^6$.

13. The method of claim 12, where R$^5$ is selected from hydrogen and —CH$_3$.

14. The method of claim 12, where R$^6$ is selected from hydrogen, —CH$_3$, and benzyl.

15. The method of claim 1, where the disease is pulmonary arterial hypertension.

16. A method of treating a patient that is in need of antiplatelet therapy, comprising administering a therapeutically effective amount of a compound of formula I:

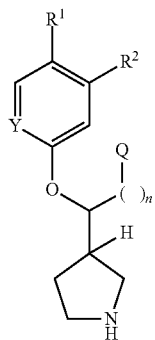

(I)

where:

Y is —CH— or —N—;

R$^1$ is selected from halo; —C$_{1-6}$alkyl optionally substituted with 1 to 5 fluoro atoms; —O—C$_{1-6}$alkyl optionally substituted with 1 to 5 fluoro atoms; —C$_{0-1}$alkylene-phenyl; —O—C$_{0-3}$alkylene-phenyl; —SO$_2$—C$_{1-6}$alkyl; —C(O)NH$_2$; and —NO$_2$;

R$^2$ is selected from hydrogen, halo, and —CN;

n is an integer from 1 to 3;

Q is selected from —NR$^3$SO$_2$R$^4$ and —SO$_2$NR$^5$R$^6$;

R$^3$ is selected from hydrogen, —C$_{1-6}$alkyl, and —C(O)C$_{1-6}$alkyl;

R$^4$ is selected from —C$_{1-6}$alkyl; —C$_{3-6}$cycloalkyl; —NR$^7$R$^5$; —CH$_2$SO$_2$—C$_{1-6}$alkyl; pyrazole optionally substituted with —CH$_3$; triazole; morpholine; benzoxadiazole; and phenyl optionally substituted with R$^9$; where R$^7$ and R$^8$ are independently selected from hydrogen and —C$_{1-6}$alkyl; and R$^9$ is selected from —CN, —COOH, —NO, —C$_{0-2}$alkylene-O—C$_{1-6}$alkyl, —C(O)NR$^7$R$^8$, —NR$^7$C(O)—C$_{1-6}$alkyl, —SO$_2$—C$_{1-6}$alkyl, —SO$_2$—NR$^7$R$^8$, and a nitrogen-containing heteroaryl optionally substituted with 1 or 2 -CH$_3$ groups;

R$^5$ is selected from hydrogen and —C$_{1-6}$alkyl; and

R$^6$ is selected from hydrogen, —C$_{1-6}$alkyl, and benzyl;

or a pharmaceutically acceptable salt thereof.

* * * * *

UNITED STATES PATENT AND TRADEMARK OFFICE
CERTIFICATE OF CORRECTION

PATENT NO. : 8,637,568 B2  
APPLICATION NO. : 13/936312  
DATED : January 28, 2014  
INVENTOR(S) : Eric L. Stangeland et al.

Page 1 of 1

It is certified that error appears in the above-identified patent and that said Letters Patent is hereby corrected as shown below:

In the Claims

At Column 60, lines 21-22,

"-$C_{1-6}$alkylene-phenyl" should be "-$C_{0-1}$alkylene-phenyl".

At Column 60, line 22,

"-SO-$C_{1-6}$alkyl" should be "-$SO_2$-$C_{1-6}$alkyl".

At Column 60, line 30,

"-$NR^7R^5$" should be "-$NR^7R^8$".

At Column 60, line 35,

"-NO" should be "-$NO_2$".

At Column 60, line 52, insert --method of-- before "claim 1".

At Column 61, line 1,

"-$SO_2NRSR^6$" should be "-$SO_2NR^5R^6$".

At Column 62, line 14,

"-$NR^7R^5$" should be "-$NR^7R^8$".

At Column 62, line 19,

"-NO" should be "-$NO_2$".

Signed and Sealed this  
Eighth Day of July, 2014

Michelle K. Lee  
*Deputy Director of the United States Patent and Trademark Office*